United States Patent
Currier, III

(10) Patent No.: US 11,207,771 B2
(45) Date of Patent: Dec. 28, 2021

(54) PROTECTIVE INTERFACE DEVICE WITH COMPLEMENTARY CASE, STAND AND SATCHEL

(71) Applicant: George Tyler Currier, III, North Brunswick, NJ (US)

(72) Inventor: George Tyler Currier, III, North Brunswick, NJ (US)

(*) Notice: Subject to any disclaimer, the term of this patent is extended or adjusted under 35 U.S.C. 154(b) by 0 days.

(21) Appl. No.: 16/950,693

(22) Filed: Nov. 17, 2020

(65) Prior Publication Data

US 2021/0291343 A1 Sep. 23, 2021

Related U.S. Application Data

(63) Continuation-in-part of application No. 29/754,380, filed on Oct. 9, 2020, which is a continuation-in-part of application No. 29/732,915, filed on Apr. 28, 2020, now abandoned.

(60) Provisional application No. 62/990,785, filed on Mar. 17, 2020, provisional application No. 63/019,169, filed on May 1, 2020.

(51) Int. Cl.
*B25G 1/10* (2006.01)
*A61L 2/10* (2006.01)
*A61L 2/26* (2006.01)

(52) U.S. Cl.
CPC ............... *B25G 1/102* (2013.01); *A61L 2/10* (2013.01); *A61L 2/26* (2013.01); *A61L 2202/11* (2013.01)

(58) Field of Classification Search
None
See application file for complete search history.

(56) References Cited

U.S. PATENT DOCUMENTS

| D208,198 S | 8/1967 | Gould |
| D215,157 S | 9/1969 | Edmondson |
| 3,866,649 A | 2/1975 | Bringmann |

(Continued)

FOREIGN PATENT DOCUMENTS

| CN | 108860278 A | 11/2018 |
| CN | 108969108 A | 12/2018 |

(Continued)

OTHER PUBLICATIONS

Shopping Cart Handle Covers—https://lookieloops.com/collections/cootie-loops Web Page Retrieved Oct. 2, 2020.

(Continued)

*Primary Examiner* — Andrew Smyth
(74) *Attorney, Agent, or Firm* — Lewis Roca Rothgerber Christie LLP

(57) ABSTRACT

The invention relates to a sanitary interface device that provides safety and mitigates risk associated with the spread of disease and illness (e.g., viruses) resulting from human contact with potentially contaminated objects such as a handle. The interface device includes a rigid, U-shaped body having a curved portion and a pair of legs projecting therefrom. The curved portion interfaces with the potentially contaminated handle, while the pair of legs shield a user's hands from the handle. The interface device can be portable and reusable, while being adapted for use as part of a kit which could also include accessories, such as a case, stand and/or satchel.

31 Claims, 22 Drawing Sheets

(56) References Cited

U.S. PATENT DOCUMENTS

| | | | |
|---|---|---|---|
| 4,305,265 A | | 12/1981 | Burgas |
| D298,077 S | * | 10/1988 | Goodwin ................ B62B 5/069 |
| | | | D34/27 |
| 4,881,746 A | | 11/1989 | Andreesen |
| 4,955,914 A | * | 9/1990 | Caniglia ................ A61J 17/113 |
| | | | 606/235 |
| D324,368 S | * | 3/1992 | Zirkelbach ................ D12/317 |
| D328,812 S | * | 8/1992 | Pritchett ................ D34/27 |
| 5,160,105 A | * | 11/1992 | Miller ................ A47B 91/04 |
| | | | 248/188.9 |
| D351,668 S | * | 10/1994 | Lim ................ D25/121 |
| 5,503,297 A | * | 4/1996 | Frankel ................ A47G 23/0225 |
| | | | 220/737 |
| D370,110 S | * | 5/1996 | Beam ................ B62B 5/069 |
| | | | D34/27 |
| 5,658,029 A | | 8/1997 | Franko |
| 5,715,571 A | | 2/1998 | Fasano |
| 5,836,322 A | | 11/1998 | Borger et al. |
| D403,540 S | | 1/1999 | Williams |
| D412,609 S | * | 8/1999 | Karp ................ D34/27 |
| D425,681 S | * | 5/2000 | Johnson ................ D34/27 |
| 6,065,764 A | * | 5/2000 | Moseley ................ B62B 5/06 |
| | | | 150/154 |
| 6,158,640 A | * | 12/2000 | Karp ................ B62B 3/1408 |
| | | | 224/277 |
| 6,817,066 B1 | * | 11/2004 | Williams ................ B62B 3/1428 |
| | | | 150/154 |
| D505,909 S | * | 6/2005 | Erskine ................ D12/317 |
| 6,926,291 B1 | * | 8/2005 | Ondrasik ................ B62B 3/1404 |
| | | | 280/33.991 |
| 6,981,707 B1 | * | 1/2006 | Dandy ................ B62B 5/06 |
| | | | 150/154 |
| D521,207 S | * | 5/2006 | Anderson ................ B62B 5/069 |
| | | | D34/27 |
| 7,104,552 B2 | | 9/2006 | Swanson et al. |
| 7,188,858 B2 | * | 3/2007 | Hartenstine ................ B62B 7/083 |
| | | | 280/642 |
| 7,213,603 B2 | | 5/2007 | Pinsky |
| 7,281,718 B2 | * | 10/2007 | Malchow ................ B62B 3/1408 |
| | | | 150/154 |
| 7,430,779 B1 | | 10/2008 | Garry |
| D635,733 S | * | 4/2011 | Willig ................ B62B 5/069 |
| | | | D34/27 |
| 8,109,524 B1 | | 2/2012 | Toohey et al. |
| D657,300 S | * | 4/2012 | Wright ................ D12/317 |
| 8,234,734 B2 | | 8/2012 | Perry |
| D689,824 S | | 9/2013 | Ng et al. |
| D707,009 S | | 6/2014 | Walter |
| D732,260 S | * | 6/2015 | Wiley ................ D34/27 |
| D743,663 S | * | 11/2015 | Hoffheimer ................ D34/27 |
| 9,534,764 B2 | | 1/2017 | Trajlinek et al. |
| D778,841 S | | 2/2017 | Seever |
| D813,487 S | | 3/2018 | Eskridge |
| D905,370 S | | 12/2020 | Poirier et al. |
| 2004/0149608 A1 | | 8/2004 | Laux et al. |
| 2006/0202438 A1 | | 9/2006 | Helmy et al. |
| 2007/0126193 A1 | * | 6/2007 | Hess ................ B62B 5/06 |
| | | | 280/33.992 |
| 2008/0191434 A1 | | 8/2008 | Herron |
| 2008/0303230 A1 | * | 12/2008 | Somberg ................ B62B 5/06 |
| | | | 280/33.992 |
| 2010/0147723 A1 | * | 6/2010 | Farrell ................ B65G 49/061 |
| | | | 206/453 |
| 2011/0011995 A1 | * | 1/2011 | Tridon De Rey ........ G09F 3/20 |
| | | | 248/214 |
| 2011/0148056 A1 | * | 6/2011 | Niernberger ............ B62B 5/069 |
| | | | 280/33.992 |
| 2011/0182769 A1 | | 7/2011 | Rich |
| 2013/0313297 A1 | * | 11/2013 | Belby ................ B62B 3/1428 |
| | | | 224/411 |
| 2014/0076757 A1 | | 3/2014 | Fredankey |
| 2016/0339937 A1 | * | 11/2016 | Dyer ................ B62B 3/1428 |
| 2017/0296856 A1 | | 10/2017 | Burke |
| 2018/0229746 A1 | * | 8/2018 | Bacallao ................ B62B 3/001 |
| 2019/0119892 A1 | | 4/2019 | Patterson et al. |
| 2019/0291764 A1 | | 9/2019 | Heiman et al. |
| 2020/0223467 A1 | | 7/2020 | Olbrich et al. |

FOREIGN PATENT DOCUMENTS

| | | |
|---|---|---|
| DE | 2453480 A1 | 5/1976 |
| GB | 2221971 A | 2/1990 |
| GB | 2271094 A | 4/1994 |
| JP | 2005289419 A | 10/2005 |
| KR | 101667162 B1 | 10/2016 |

OTHER PUBLICATIONS

NICEMEET 4PCS/Pack Universal Protective Covers for Baby Cart Handle, Baby Stroller Armrest Leather Cover, Armrest Handle Covers—https://www.amazon.ca/NICEMEET-Universal-Protective-Stroller-Armrest/dp/B07WZFJS32 Web Page Retrieved Oct. 2, 2020.

Kleangrips—https://kleangrips.com/collections/all Web Page Retrieved Oct. 2, 2020.

CART CUFF Shopping Cart Handle Cover Protects Hands from Germs—https://www.amazon.com/Shopping-Handle-Cover-Protects-Hands/dp/B007S07GN4/ref=redir_mobile_desktop?ie=UTF8&%2AVersion%2A=1&%2Aentries%2A=0 Web Page Retrieved Oct. 9, 2020.

Design U.S. Appl. No. 29/732,915, filed Apr. 28, 2020, entitled "Protective Interface Device."

Design U.S. Appl. No. 29/754,380, filed Oct. 9, 2020, entitled "Protective Interface Device."

Google search Feb. 23, 2021, Handle Pop, https://coolmompicks.com/blog/2020/07/07/handle-pop-silicone-supermarket-cart-handle/ (Year: 2021).

Google search Amazon, Feb. 23, 2021, dbest products Germ Guard, /www.amazon.com/dbest-products-Contactless-Supermarket-Alternative/dp/B087ZRZFCD?th=1 (Year: 2021).

Google search, Klean Grips, Feb. 23, 2021, https://klean-grips.squarespace.com/new-products (Year: 2021).

PCT International Search Report and Written Opinion for PCT/US2020/060911 entitled "Protective Interface Device With Complementary Case, Stand and Satchel" dated May 3, 2021, 17 pages.

U.S. Appl. No. 17/187,342, filed Feb. 26, 2021 entitled "Protective Interface Device With Complementary Case, Stand and Satchel".

U.S. Appl. No. 17/187,461, filed Feb. 26, 2021 entitled "Protective Interface Device With Complementary Case, Stand and Satchel".

* cited by examiner

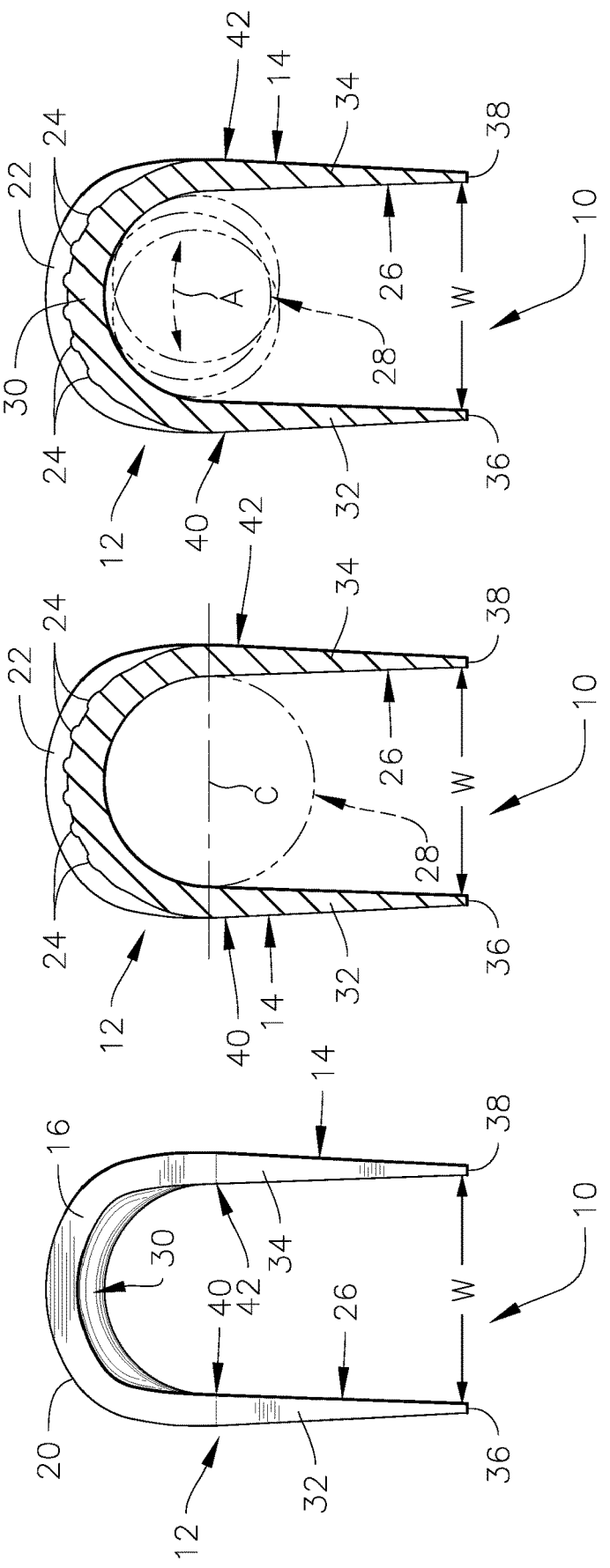

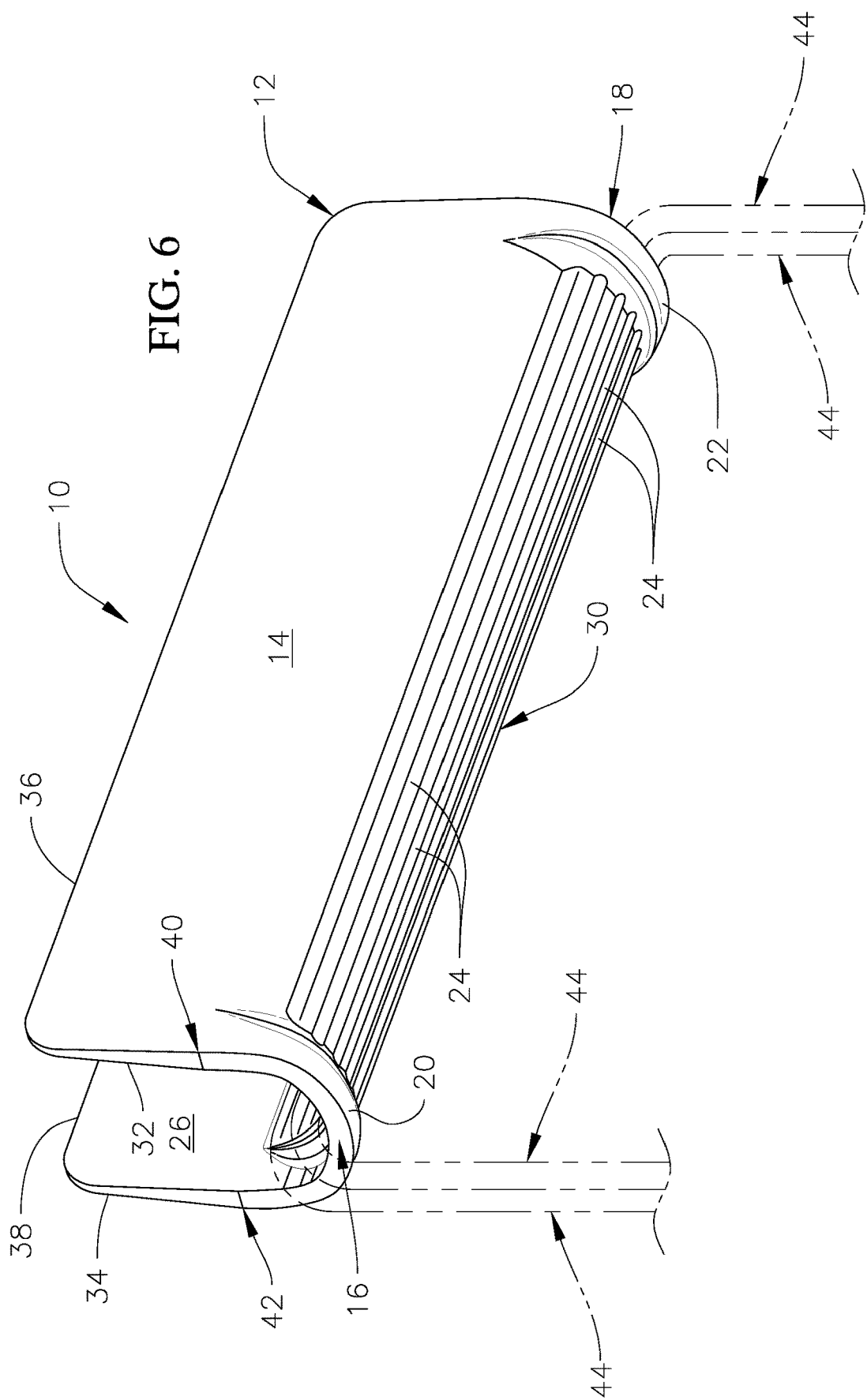

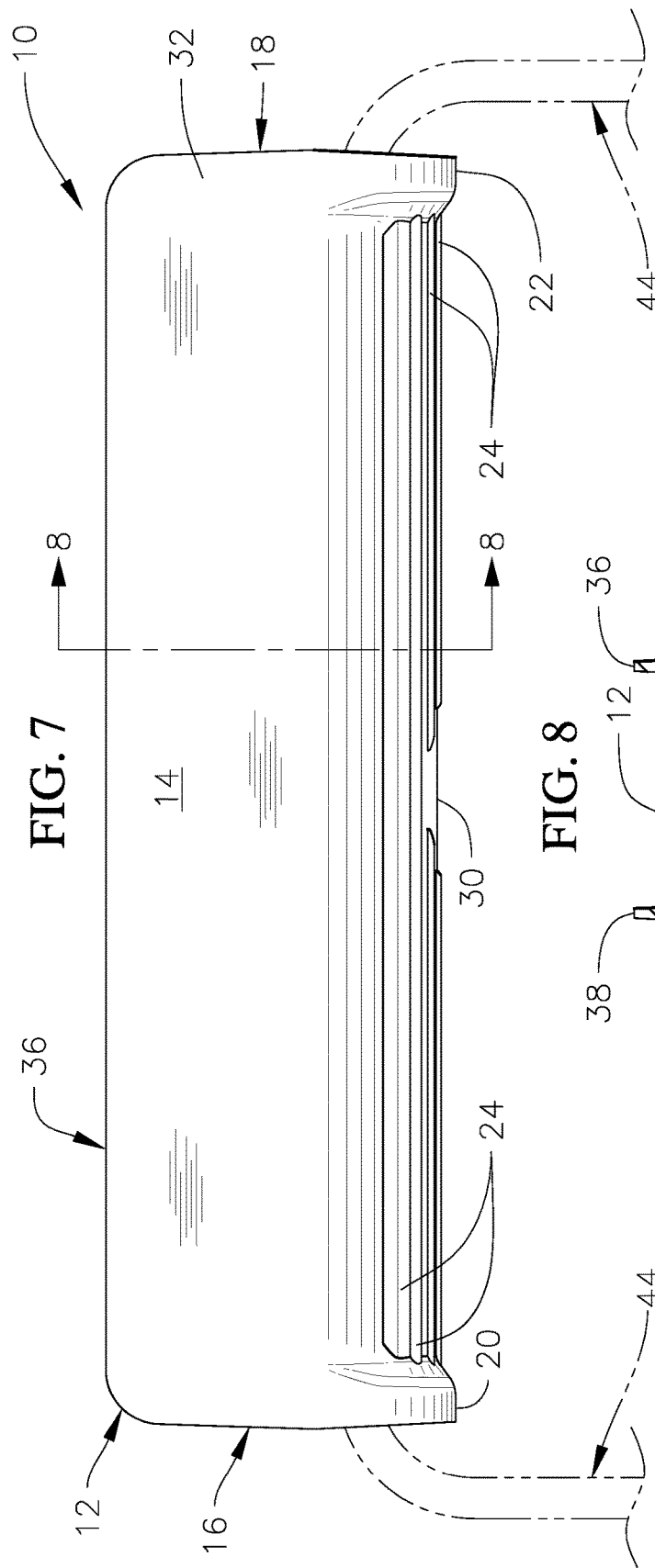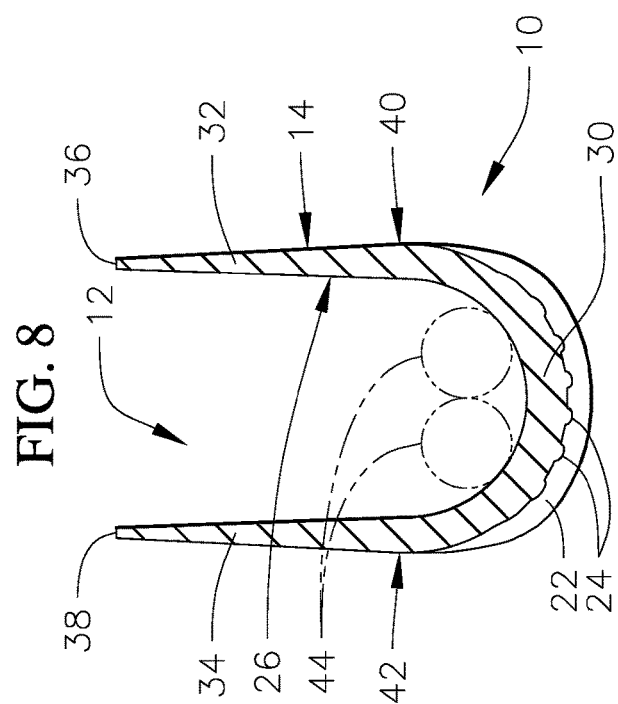

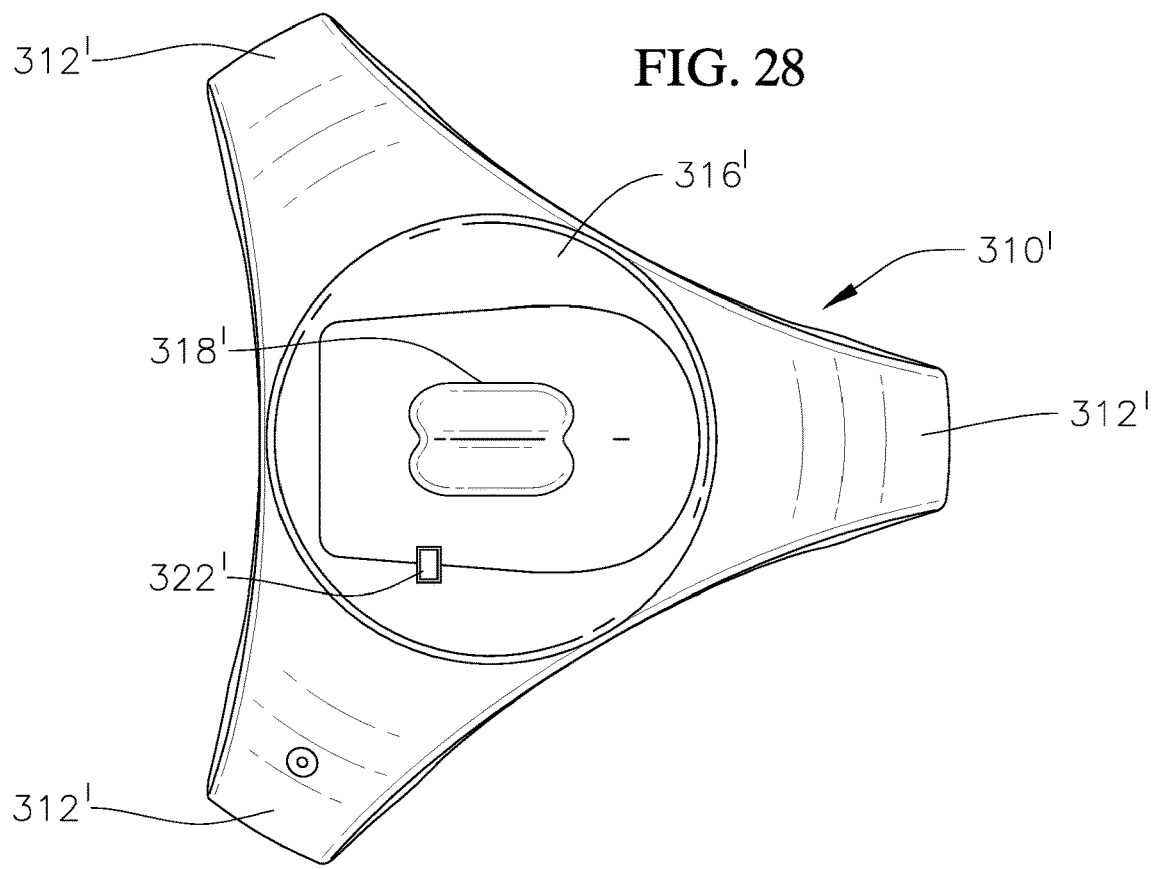
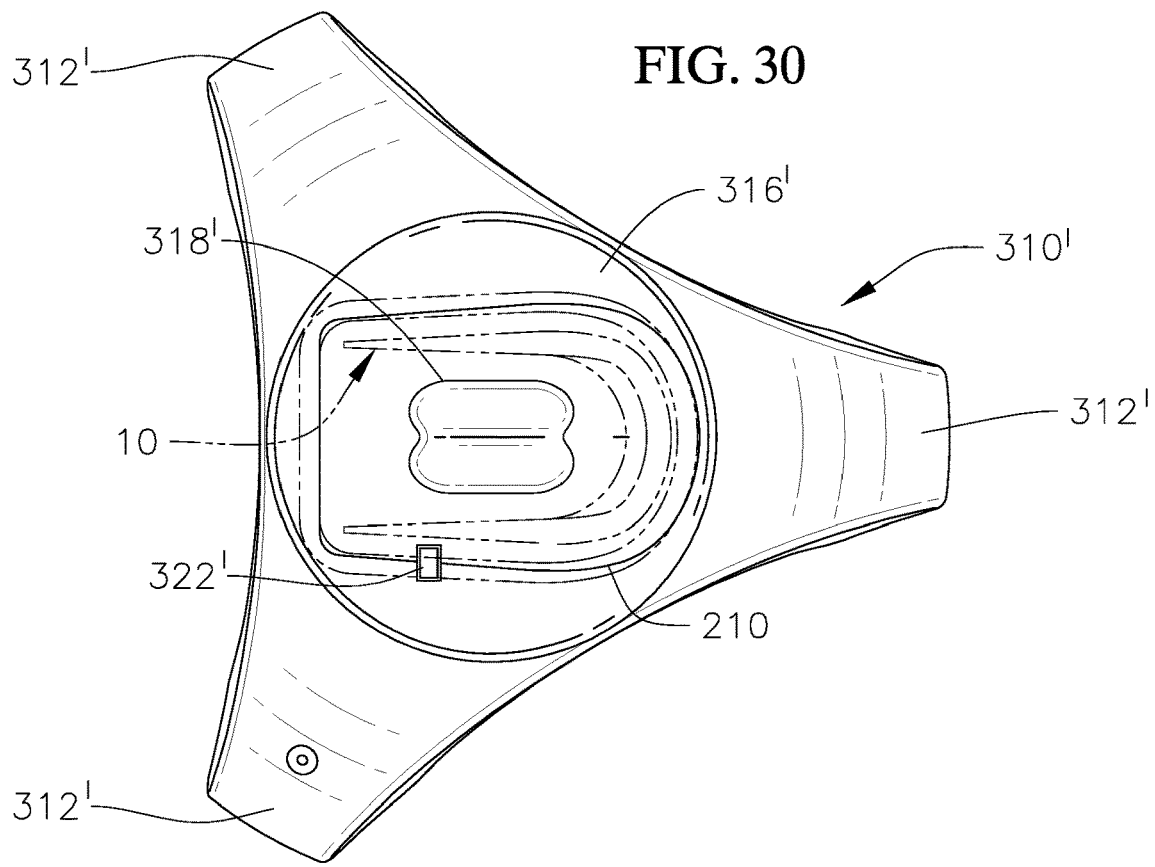

PROTECTIVE INTERFACE DEVICE WITH COMPLEMENTARY CASE, STAND AND SATCHEL

CROSS-REFERENCE TO RELATED APPLICATIONS

This application claims priority to U.S. Provisional Patent Application Ser. No. 62/990,785 filed Mar. 17, 2020, and U.S. Provisional Patent Application Ser. No. 63/019,169 filed May 1, 2020, and is a continuation-in-part of U.S. Design patent application Ser. No. 29/754,380 filed Oct. 9, 2020, which application is a continuation-in-part of U.S. Design patent application Ser. No. 29/732,915, filed Apr. 28, 2020 (now abandoned), the collective disclosures of all of which applications are incorporated herein by reference.

FIELD OF THE INVENTION

The present invention relates to health and safety products. More particularly, it relates to adapters, in the form of a handle grip, and accessories therefor that an individual can use to minimize the potential for contact with surfaces potentially supporting germs and/or pathogens, or that are otherwise potentially contaminated.

BACKGROUND OF THE INVENTION

In recent years, an increased emphasis on public health has been seen. The threats of bioterrorism and pandemics have brought health and safety concerns to the forefront of public perception. To combat these threats, a variety of consumer products have been developed. For example, gloves, disinfectant wipes, hand sanitizers, anti-microbial soaps and the like have been used to prevent the spread of potential pathogens, such as viruses and bacteria. These conventional protective measures are (i) generalized, (ii) require application for every interaction in order to be even somewhat effective and (iii) possess undesirable characteristics that are not readily apparent to the average user.

To be effective, many disinfectants must remain wet on the surface for up to 15 minutes. Ignorant and impatient users often apply the disinfectant to the contaminated surface, immediately wipe it dry and then contact the still contaminated surface with food, medications, or their body.

Contaminated gloves are typically disposed of, rather than cleaned. A hidden shortcoming with disposable gloves comes when the gloves are being removed and the snapping action of the rubber sprays the contamination onto the user's face, eyes, and other unprotected areas.

The foregoing shortcomings of the prior art discussed above become especially problematic during public health crises such as the aforementioned pandemics. Hence, there exists a need for products that directly address the points of contact that pose the most risk of injury or transmission of disease and illness.

SUMMARY OF THE INVENTION

The present invention is a protective interface device that is adapted specifically for minimizing risks associated with public or shared objects that offer the possibility of being contaminated with pathogens, viruses, bacteria, or chemical, biological or radioactive contaminants. In use, the device inhibits a user's direct manual contact with the handles of conventional shopping carts, material carts, luggage handles, jail cell doors, briefcases, gym bags, tubular door handles, refrigerated beverage cases, shopping baskets, etc. The present invention can also be used on ships to open doors, or on planes to manage tray tables or open and close overhead compartments.

In various embodiments, the invention involves single layer or multi-layer interface devices in the form of a handle grip configured to cover, at least partially, a handle or other object that may be contaminated. The handle grip is multi-positionable and adapted for interchangeable use with a plurality of different handles. An open-ended, trough-like shape, in one particular embodiment, enables the interface device (i.e., handle grip) to be applied to potentially contaminated objects (e.g., the handles of shopping carts, material carts, luggage and shopping baskets) in a "top-grip" position, a "bottom-grip" position or a "side-grip" position, depending upon the type of handle the device is applied to. As used above and throughout this application, the terms "interface device" and "handle grip" are synonymous and therefore interchangeable for purposes of describing the present invention.

Whether applied in a "top-grip" position, a "bottom-grip" position or a "side-grip" position, the interface device has, in one particular embodiment, a generally "U"-shaped outer surface which can be substantially rigid or flexible, but in either case adapted and configured to be gripped by the hand or hands of a user. For the purposes of the present application, "substantially rigid" will refer to a handle grip, or its material, that is resistant to deformation and substantially retains its original shape in operation and typical use. A generally "U"-shaped inner surface of the device can be rigid or flexible, but in either case adapted and configured to directly engage the potentially contaminated object, such as a shopping cart, material cart, luggage, or shopping basket handle. The interface device has a wall thickness, measured between the outer and inner surfaces, sufficient to create a barrier or buffer between the user's hand or hands and the potentially contaminated object, whereby the user's hand or hands do not need to come into direct contact with such object.

In one embodiment, the handle grip has a central body having an outer surface that is grippable by a user, and an inner surface configured to be at least partially contactable with a potentially contaminated handle or other potentially contaminated surface. The outer and inner surfaces are defined by a pair of substantially straight and substantially parallel legs extending from opposite sides of a central body section bridging between the legs. "Substantially straight" and "substantially parallel" properties are defined by lack of visible angles or bends and general symmetry in the legs relative to the body, respectively.

With the foregoing definitions in mind, the legs of the aforementioned handle grip are spaced apart along their entire lengths and terminate remote from the central body section in non-deflectable free ends which cooperate to define an open mouth of a predetermined, substantially fixed dimension (i.e., lateral width) selected to permit the handle grip to be applied to and removed from a potentially contaminated handle by a user without wrapping the legs around the contaminated object, and without increasing or decreasing the dimension of the mouth especially during removal. In other words, the non-deflectable free ends do not move relative to one another when the interface device makes contact with a potentially contaminated surface. In an embodiment, the lengths of the legs are selected so as to inhibit a user and/or third party from contacting the potentially contaminated handle to which the handle grip is applied. Put another way, the legs have lengths which position the open mouth distal to (i.e., remote from) the potentially contaminated handle, thereby inhibiting a user from contacting the potentially contaminated inner surface of the handle grip with his or her hands when applying the handle grip to, or removing the handle grip from, the potentially contaminated handle or other surface. In other words, the lengths of the handle grip's legs and consequent remote positioning of the handle grip's open mouth cooperate to protect a user from inadvertently contacting not only the potentially contaminated handle, but also the potentially contaminated inner surface of the handle grip itself especially during removal.

In use, the interface device may be applied to a horizontally-oriented handle such that the mouth of the handle grip is in a downward facing orientation, whereby the handle grip itself is in a "top-grip" position. The interface device is designed such that it can be applied to other horizontally-oriented handles with its mouth in an upward facing orientation, whereby the handle grip itself is in a "bottom-grip" position. The interface device can also be applied to a vertically-oriented handle such that its mouth is in a sideways facing orientation, whereby the handle grip itself is in a "side-grip" position.

The interface device may be adapted for use with a carrying/storage/treatment case, which itself can be adapted to envelop the interface device, especially the embodiment having the unique "U"-shaped cross-sectional configuration. In other words, the case can be configured to removably receive the handle grip. Once the device is stowed therein and the case is closed, such as by shutting a lid at an open end, the case provides a protective barrier between a potentially contaminated interface device and a user's hands or the hands of third parties. The case can be adapted to contain disinfectant or other cleaning means in order to sanitize or otherwise treat a contaminated device placed therein. To enhance such cleaning functionality, the lid or other sealing means can be provided with a fluid-tight seal.

The case and interface device are adapted to cooperate with a specialized stand configured to receive one or more cases that may contain either a contaminated or sanitized interface device. The stand may be portable for added convenience. For instance, the stand can have a docking station configured to receive a case adapted to store handle grips. In another embodiment, the stand has a receptacle configured to removably receive an end of said case such that said case is maintained in a generally upright orientation when the case is received in the stand. Together with the case and stand, the handle grip can form an associated kit. Alternatively, the handle grip(s) and case could constitute a kit by themselves.

In certain embodiments, an ultraviolet radiation (UV) source is included in the stand to sanitize, disinfect or otherwise treat a handle grip contained in an associated case, which can be simultaneously sanitized, disinfected or otherwise treated by the UV source. The source of ultraviolet radiation can also be configured to be positionable between the legs of a U-shaped handle grip contained within a case which is docked or otherwise received in the stand.

The handle grip(s), case(s) and/or stand(s) described hereinabove can be used separately or sold and used as a set or kit. In one embodiment, multiple handle grips can constitute a kit. In another embodiment, handles of varying sizes can constitute the kit, including handle grips with a first length (e.g., elongated handle grips) and handle grips with a second length (e.g., non-elongated handle grips) shorter than the first length. In another embodiment, the kit comprises one or more cases and one or more handle grips. In a further embodiment, the kit can comprise a case, a stand and one or more handle grips. The kit's handle grip, case and stand can be used in cooperation with a decontamination agent, which can be any compound or means (e.g., chemicals or radiation) by which the kit components can be cleansed, sanitized, decontaminated and/or otherwise treated. Needless to say, the handle grip and the case must be compatible with the decontamination agent, for the purposes of safety. In yet another embodiment, a satchel for the case or cases can be provided as part of any of the aforementioned kits that employ at least one case.

In one embodiment, a non-contact method for a user to interface with a potentially contaminated surface using the aforementioned kit(s) involves, for example, the steps of inserting the handle grip into the interior chamber of the case; treating the handle grip with a decontamination agent while the handle grip is in the case; removing the handle grip from the case after the handle grip has been treated; placing the treated handle grip on a potentially contaminated surface; removing the treated handle grip from the potentially contaminated surface, the handle grip thereby being potentially contaminated; stowing the potentially contaminated handle grip in the case; and re-treating the handle grip with a decontamination agent while the handle grip is in the case. The treatment and re-treatment steps may be performed in the case's interior chamber, whereby the case's interior chamber is treated simultaneously together with any and all handle grips contained therein.

In a further embodiment, a non-contact method for a user to interface with a potentially contaminated surface using the aforementioned kit(s) involves, for example, the steps of inserting the handle grip into the interior chamber of the case; setting the case in a stand; treating the handle grip with a decontamination agent while the handle grip is in the case; removing the case from the stand after the handle grip has been treated; removing the handle grip from the case after the handle grip has been treated; placing the treated handle grip on a potentially contaminated surface; removing the treated handle grip from the potentially contaminated surface, the handle grip thereby being potentially contaminated; stowing the potentially contaminated handle grip in the case; transporting the case to a location where the stand is situated; setting the case in the stand; and re-treating the handle grip with a decontamination agent while the handle grip is in the case and while the case is in the stand. The treatment and re-treatment steps may be performed in the case's interior chamber, whereby the case's interior chamber is treated simultaneously together with any and all handle grips contained therein.

Furthermore, in yet another embodiment, a method for decontaminating potentially contaminated handle grips using the UV-equipped stand detailed hereinabove involves, for example, the steps of placing a potentially contaminated handle grip in the interior chamber of a case; placing the case in the stand such that the interior chamber of the case and the handle grip are exposable to UV radiation emitted from a source of the UV radiation; and actuating the UV radiation source for a length of time and intensity sufficient to sanitize or otherwise treat the handle grip as well as the interior chamber of the case. To this end, the UV source can extend into the interior chamber of the case and be located in proximity to the potentially contaminated handle grip(s).

BRIEF DESCRIPTION OF THE FIGURES

For a more complete understanding of the present invention, reference is made to the following detailed description of various representative embodiments considered in conjunction with the accompanying drawings, in which:

FIG. 3 is an end view of the interface device shown in FIGS. 1 and 2;

FIG. 4 is a lateral cross-sectional view taken along cross-section line 4-4 of FIG. 2 and looking in the direction of the arrows, of the interface device shown in FIGS. 1 and 2;

FIG. 5 is a lateral cross-sectional view similar to FIG. 4, but showing the inventive interface device positioned on a shopping cart handle having a diameter smaller than that of the shopping cart handle depicted in FIG. 4;

FIG. 6 is a perspective view of the interface device of FIG. 1, the interface device being shown in a "bottom-grip" position for use on a dual handle of a shopping basket, which is shown in phantom;

FIG. 7 is a side elevational view of the interface device shown in FIG. 6;

FIG. 8 is a lateral cross-sectional view, taken along section line 8-8 of FIG. 7 and looking in the direction of the arrows, of the interface device shown in FIGS. 6 and 7;

FIG. 28 is a top plan view of the stand of FIG. 26;

FIG. 30 is a top plan view of the stand, case and handle grip of FIG. 29, the latter two components of the combination being shown in phantom.

DETAILED DESCRIPTION OF VARIOUS EMBODIMENTS

Figure 1:
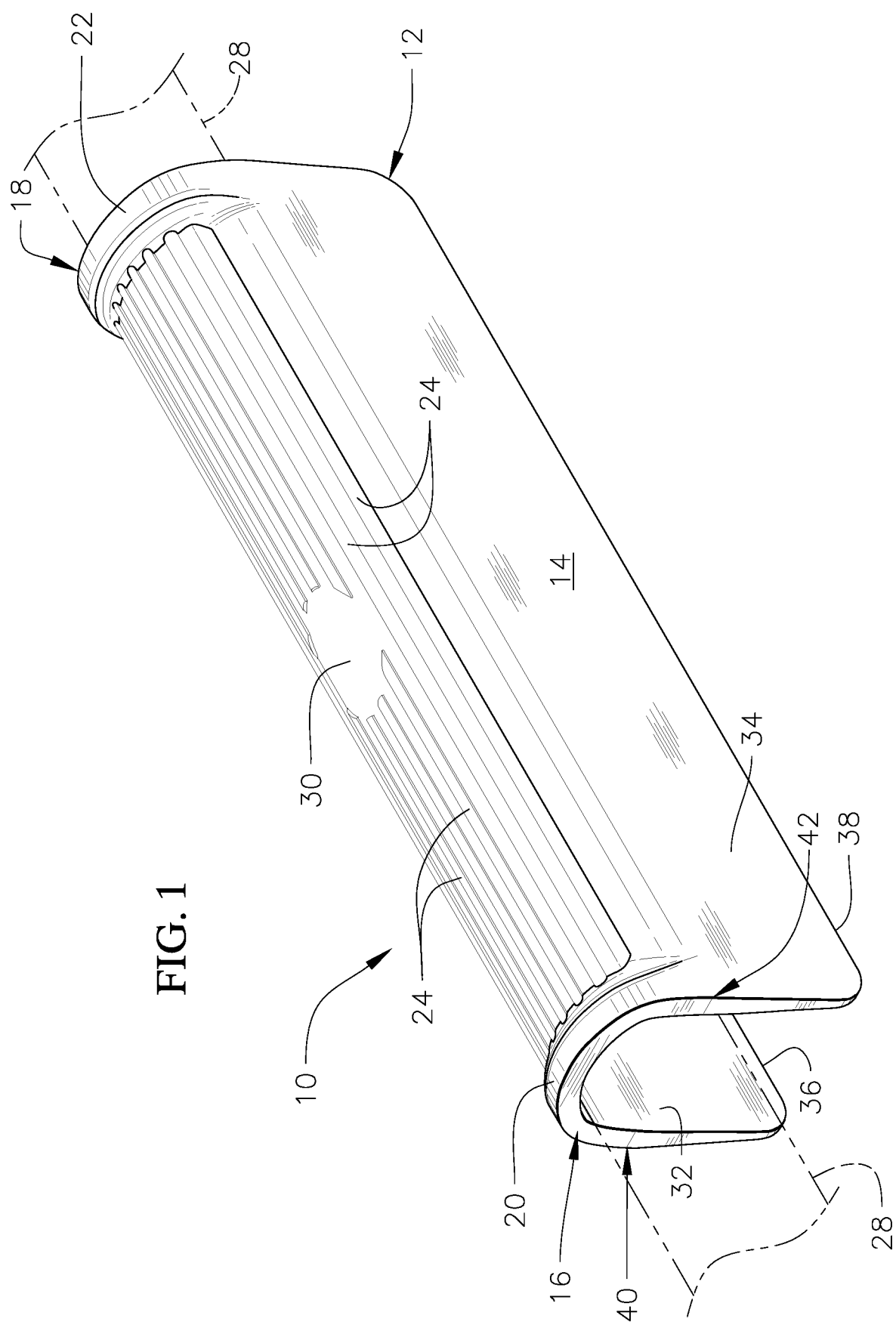
FIG. 1 is a perspective view of an interface device in accordance with one embodiment of the present invention, the interface device being shown in a "top-grip" position for use on a shopping cart handle, which is depicted in phantom.

Embodiments will now be discussed in more detail referring to the drawings that accompany the present application. In the accompanying drawings, various embodiments are illustrated. It is to be understood, however, that these embodiments are merely illustrative of the invention, which can be embodied in various forms. In addition, the specific features of the illustrated embodiments are intended to be illustrative, and not restrictive. Further, the figures are not necessarily to scale, and some features may be exaggerated to show details of particular components with the understanding that sizes, materials and similar details shown in the figures are intended to be illustrative and not restrictive. Therefore, specific structural and functional details illustrated in the accompanying drawings are not to be interpreted as limiting, but merely as a representative basis for teaching one skilled in the art how to make and use the embodiments disclosed and illustrated herein.

Subject matter will also be described in the following text with reference to the accompanying drawings. The subject matter described hereinafter may, however, be embodied in a variety of different forms and, therefore, such subject matter should not be construed as being limited to any of the exemplary embodiments described herein. Among other things, for example, the disclosed subject matter may be embodied in the form of methods, devices, components, systems and/or combinations thereof. The following detailed description is, therefore, not intended to be taken in a limiting sense.

Throughout the specification, terms may have nuanced meanings suggested or implied in context beyond an explicitly stated meaning. Likewise, the phrase "in one embodiment" as used herein does not necessarily refer to the same embodiment and the phrases "in another embodiment" and "other embodiments" as used herein do not necessarily refer to a different embodiment. It is intended, for example, that the disclosed subject matter includes combinations of the exemplary embodiments, in whole or in part.

In general, terminology may be understood, at least in part, from usage in context. For example, terms, such as "and," "or," or "and/or," as used herein may include a variety of meanings that may depend, at least in part, upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

With the foregoing prefatory comments in mind, what follows is a detailed description of various exemplary embodiments of a protective interface device (i.e., handle grip) for minimizing inadvertent contact with germs, pathogens and other potential contaminants. In one exemplary embodiment, the device has a generally "U"-shape that permits the device to be placed on, under, or on the side of an object, such as a bar or handle, which poses a potential risk of transmission of pathogens, such as by virtue of being in a public space. In an embodiment, the device is especially adapted for use with any object having a handle, including but not limited to conventional shopping carts, material carts, luggage, shopping baskets, or any bar-like object that a user can grab, pull or lift. However, it will be appreciated that other embodiments of the device can be adapted for use in connection with a variety of different objects, such as doorknobs, levers, push buttons, touch-sensitive screens and the like.

Figure 2:
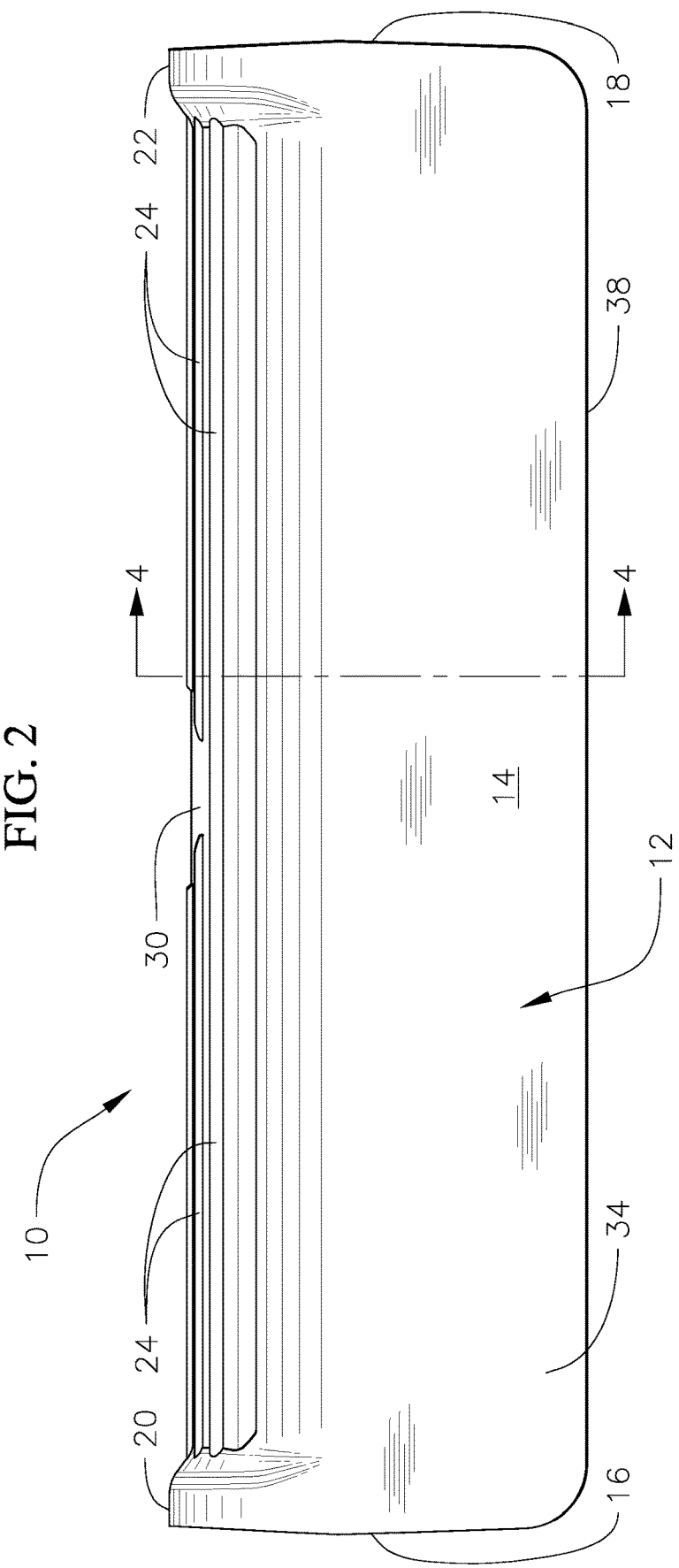
FIG. 2 is a side elevational view of the interface device shown in FIG. 1.

Referring now to FIGS. 1-3, a protective interface device 10 (i.e., handle grip) is shown in a "top-grip" position. The device 10 comprises an elongated, single layer (i.e., monolithic) body 12 made from shapeable materials, including paper, cardboard, wood, metal, leather, stiffened cloth, rubber or conventional polymeric compounds (e.g., PET, PETG or other chemically resistant thermoplastic). The body 12 possesses a generally "U"-shaped outer surface 14 adapted to be held by the user or otherwise come into contact with a user's hand or hands. The body 12 has a pair of opposed ends 16, 18, each of which includes a corresponding one of a pair of guard-rails 20, 22, respectively, whose functions will be described hereinafter. A plurality of ribs 24 extend along the outer surface 14 of the body 12 between the guard-rails 20, 22. The function of the ribs 24 will be described hereinafter as well. However, it should be understood that the ribs 24 could also have a variety of different orientations relative to the outer surface 14 of the body 12. For example, the ribs 24 could extend laterally (e.g., at 90 degrees) across the outer surface 14 (see, for instance, U.S. design patent application Ser. Nos. 29/732,915 and 29/754,380, both of which applications have been incorporated herein by reference) or at any other desired angle. The ribs 24 can be made of the same material as the body 12 or a different material. It is also possible to provide each of the ribs 24 with a rubber overlay (not shown) to enhance tactile qualities when the interface device 10 is in use, as will be described hereinafter as well. In another alternate embodiment, the outer surface 14 could be rendered substantially smooth by eliminating the ribs 24 (see, for instance, U.S. design patent application Ser. Nos. 29/732,915 and 29/754,380, both of which applications have been incorporated herein by reference).

Referring still to FIGS. 1-3, a generally "U"-shaped inner surface 26 is partially surrounded by outer surface 14. Inner surface 26 is adapted to directly interface with the object of interest (e.g., a potentially contaminated object). Because of the nested design of the outer and inner surfaces 14, 26, respectively, the user is able to grip the outer surface 14 without touching or otherwise coming into contact with the inner surface 26 or the object to which the device 10 is applied. In other words, the interface device 10 serves as a physical barrier between the user and the potentially contaminated object. In its "top-grip" position, device 10 is adapted to be placed over a conventional shopping cart handle 28 (shown in phantom in FIGS. 1 and 4), via a loose fit (i.e., gravity), an interference fit or a friction fit.

Regardless of the type of fit, the device 10 is sized and shaped such that it can be slipped on and off the shopping cart handle 28 in a manner described in greater detail hereinbelow. With particular reference to FIG. 3, its "U"-shaped, open-ended design provides the device 10 with a curved, crown-like portion 30 and a pair of straight, skirt-like legs 32, 34 depending (i.e., projecting) therefrom in substantially parallel fashion. The curved portion 30 and the legs 32, 34 are configured such that the inner surface 26 of the device 10 contacts not more than half of the perimeter of the shopping cart handle 28 (see FIG. 4), thereby minimizing the total contact area between the device 10 and the shopping cart handle 28 when in use. Regulating such contact area can be accomplished by selectively configuring the inner surface 26, especially in the vicinity of the curved portion 30. For instance, the curved portion 30 could have an arcuate shape, an elliptical-like shape, a curvilinear-like shape, a parabolic-like shape or have a radius greater than the radius of the shopping cart handle 28 (see, for example, FIG. 5), as well as having any other non-complementary shape relative to the shopping cart handle 28 or any other object to which the device 10 is applied. As a result, in certain embodiments, only portions of inner surface 26 are contactable with a handle to which the device 10 is applied.

The cross-sectional shapes (i.e., profiles) of the outer surface 14 and inner surface 26 can be tailored to achieve a variety of design objectives. For instance, when the inner surface 26 has a slight ellipticity (see, for example, FIG. 3 of U.S. provisional patent application Ser. No. 63/019,169, which application has been incorporated herein by reference), rotation about the shopping cart handle 28 will be facilitated. This is due to an inherent reduction of contact area, and consequent reduction of friction between the shopping cart handle 28 and the handle grip 10. Such a shape also enhances a user's ability to adjust the handle grip 10 to the angle of their preferred grip position when the handle grip 10 is in use. In the case of the outer surface 14, a generally elliptical shape may provide superior comfort to a user.

The legs 32, 34 are spaced apart along their entire lengths and terminate remote from the central body section 12 in non-deflectable free ends 36, 38, respectively, which cooperate with each other to define an open mouth of a predetermined, substantially fixed dimension (i.e., lateral width) "W" (see FIGS. 3-5) selected to permit the handle grip 10 to be applied to and removed from a potentially contaminated handle by a user without wrapping the legs 32, 34 around the contaminated object, and without increasing or decreasing the dimension of the mouth. In other words, the non-deflectable free ends 36, 38 do not move relative to one another when the interface device 10 makes contact with a potentially contaminated surface. In an embodiment, the lengths of the legs 32, 34 are selected so as to inhibit a user and/or third party from contacting the potentially contaminated shopping cart handle 28 to which the handle grip 10 is applied. At approximate locations 40, 42, the legs 32, 34, respectively, merge into the curved portion 30 of the body 12.

By way of example, the inner surface 26 can have a first contactable portion configured to be contacted by the shopping cart handle 28, which portion constitutes part of the curved portion 30 of the body 12, and second and third contactable portions configured to be contacted by the shopping cart handle 28, each of which portions constitutes part of a corresponding one of the legs 32, 34. The first, second and third contactable portions can simultaneously contact the shopping cart handle 28 to essentially form three tangential points of contact (see, for example, FIG. 3 of U.S. provisional patent application Ser. No. 63/019,169, which application has been incorporated herein by reference), or they can be independently contactable. As a further example, the first and second contactable portions can contact the shopping cart handle 28 in one position of the body 12 relative to the shopping cart handle 28, while the first and third contactable portions can contact the shopping cart handle 28 in another position of the body 12 relative to the shopping cart handle 28 (see, for example, FIG. 5).

In an embodiment, the body 12 is elongated and the inner surface 26 has a lateral cross-sectional shape that is non-conforming with respect to the shopping cart handle 28. In this sense, the term "non-conforming" refers to a condition in which the device 10 does not deform, stretch or otherwise change shape visibly in response to its application to or removal from the shopping cart handle 28. The device 10 can have a lateral cross-sectional shape such that its inner surface 26 is configured to present a cam-like profile to the shopping cart handle 28 to which the device 10 is applied (see FIG. 5). As shown in FIG. 4, the curved portion 30 of the device 10 can have a radius that is substantially the same as that of the shopping cart handle 28, thereby resulting in a relatively tight fit. The lateral cross-sectional shape of the inner surface 26 of the body 12 can also be flat, for use with a generally curved outer shape of a handle to which the device 10 is applied, or the inner surface 26 could be generally curved (as shown in FIGS. 3-5, for instance) for use with a flat handle (not shown). As shown in FIGS. 1-8, the body 12 and both its outer and inner surfaces 14, 26, respectively, can have lateral cross-sectional shapes that are generally U-shaped.

To inhibit a user's fingers from wrapping around the device 10 and contacting the bottom exposed surface of the shopping cart handle 28, legs 32, 34 of the body 12 have a length sufficient to allow them to perform a shielding function. This shielding function is also accomplished in that legs 32, 34 are adapted to engage a portion of the shopping cart adjacent its shopping cart handle 28 upon rotation of the device 10 about the shopping cart handle 28, thereby inhibiting inadvertent or accidental removal of the device 10 from the shopping cart handle 28. Needless to say, the legs 32, 34 are also designed to inhibit a third party, such as an infant seated in the shopping cart, from accidentally touching the exposed, potentially contaminated bottom surface of the shopping cart handle 28.

The legs 32, 34 also function to lower the center of gravity of the device 10, thereby enhancing its stability when applied to, for instance, the shopping cart handle 28 and inhibiting its inadvertent or accidental removal therefrom when in its "top-grip" position. When the handle grip 10 has a center of gravity that is below center line "C" (see FIG. 4) of shopping cart handle 28, or below the potentially contaminated surface in general, this function will be facilitated. Specifically, if rotated, either intentionally or inadvertently, the handle grip 10 would be biased back toward a "top-grip" position, thereby inhibiting accidental removal of the handle grip 10 from the shopping cart handle 28. The center of gravity can be regulated, by way of example, through mass distribution (e.g., weights near the free ends 36, 38 of the legs 32, 34, respectively), variations of shape, variations in material, and/or variations in the thicknesses of the curved portion 30 and the legs 32, 34 of the body 12.

Referring now to FIGS. 4 and 5, cross-sectional views of the interface device 10 are shown. As previously mentioned, the body 12 of the device 10 can be rotated with respect to the shopping cart handle 28. The body 12, in certain embodiments, can also be movable in a lateral direction (see the arrows "A" in FIG. 5) and/or a longitudinal direction with respect to the shopping cart handle 28 to which it is applied. During such movement of the device 10, but especially its longitudinal movement, the guard-rails 20, 22 inhibit the user's hand(s) from sliding off the body 12 and contacting the potentially contaminated shopping cart handle 28. The guard rails 20, 22 also serve to protect the user from incidental contact with the shopping cart handle 28 by providing a tactile "warning" to the user that he or she has reached one of the ends 16, 18 of the protective interface device 10.

Referring now to FIGS. 6-8, the same device 10 of FIGS. 1-5 is shown, but in a "bottom-grip" or "inverted" position. Oriented as such, the device 10 is suitable for interfacing with shopping basket handles 44 (shown in phantom in FIGS. 6-8). In contrast to the orientation shown in FIGS. 1-5, the device 10 would be placed underneath the handle 28 in a "bottom-grip" position, as opposed to the "top-grip" position depicted in FIGS. 1 and 2 in use with the shopping cart handle 28. To further adapt the device 10 to multiple uses, its dimensions can be selected to accommodate the size and shape of both the shopping cart handle 28 and the shopping basket handles 44 or any other surface with which the user wishes to interface. Regarding such other surfaces, a "side-grip" position of the device 10 allows it to protect a user when gripping vertically oriented objects, such as the handles on beverage cases or building doors. Thus, the device 10 is useable with these and other types of handles when its body 12 is in an upright orientation (i.e., a "side-grip" position"), while also being useable with some types of horizontally oriented handles when said mouth is oriented upward (i.e., in a "bottom-grip" position) and with other types of horizontally oriented handles when its mouth is oriented downward (i.e., in a "top-grip" position).

When the user's interaction with the potentially contaminated object has ended, the interface device 10 can be removed and sanitized and/or decontaminated for purposes of reuse. As the device 10 can be decontaminated, unlike other forms of protection, the device 10 is reusable (i.e., not disposable). In other words, device 10 is portable and adapted for personalized use by a single individual or a family of users.

Figure 9:
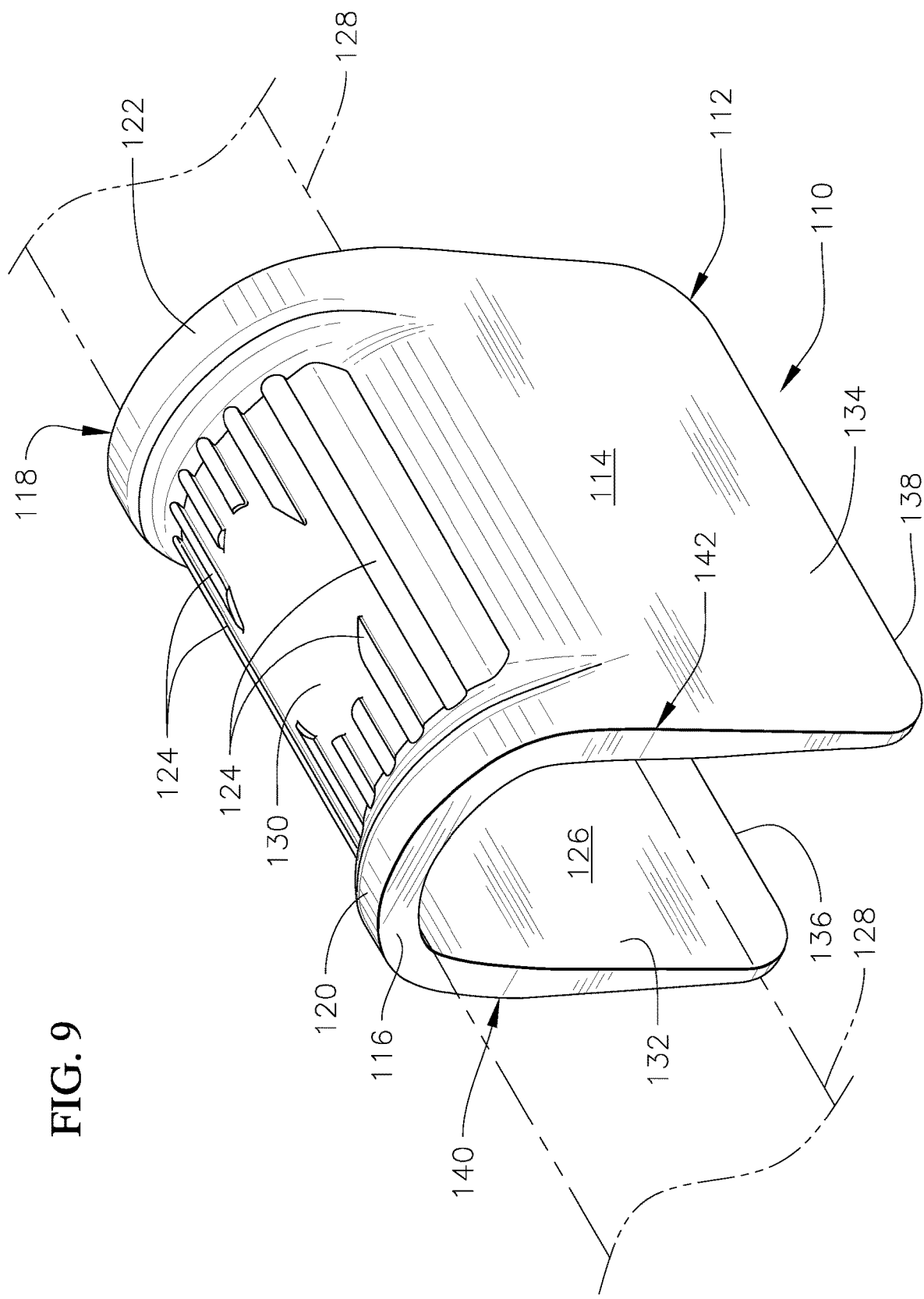
FIG. 9 is a perspective view of a shorter-length interface device in accordance with another embodiment of the present invention, the interface device being shown in a "top-grip" position like the position of the handle grip depicted in FIG. 1.

FIG. 9 shows a protective interface device (i.e., handle grip) 110, which is a shorter version of the handle grip 10 illustrated in FIGS. 1-8 and described in detail hereinabove. Due to its shorter length, the device 110 is especially adapted for use with smaller handles, such as those on doors or refrigerators. Elements of the handle grip 110 that correspond to elements of the handle grip 10 have the same reference numbers as used in FIGS. 1-8, incremented by one hundred.

With continuing reference to FIG. 9, a protective interface device 110 (i.e., handle grip) is shown in a "top-grip" position. The device 110 comprises an elongated, single layer (i.e., monolithic) body 112 made from shapeable materials, including paper, cardboard, wood, metal, leather, stiffened cloth, rubber or conventional polymeric compounds (e.g., PET, PETG or other chemically resistant thermoplastic). The body 112 possesses a generally "U"-shaped outer surface 114 adapted to be held by the user or otherwise come into contact with a user's hand. The body 112 has a pair of opposed ends 116, 118, each of which includes a corresponding one of a pair of guard-rails 120, 122, respectively, whose functions were described hereinabove. A plurality of ribs 124 extend along the outer surface 114 of the body 112 between the guard-rails 120, 122. Other features of the ribs 124, as well as their functionality, were described hereinabove.

A generally "U"-shaped inner surface 126 is partially surrounded by outer surface 114. Inner surface 126 is adapted to directly interface with the object of interest (e.g., a potentially contaminated object). Because of the nested design of the outer and inner surfaces 114, 126, respectively, the user is able to grip the outer surface 114 without touching or otherwise coming into contact with the inner surface 126 or the object to which the device no is applied. In other words, the interface device 110 serves as a physical barrier between the user and the potentially contaminated object. In its "top-grip" position, device no is adapted to be placed over a conventional shopping cart handle 128 (shown in phantom in FIG. 9), via a loose fit (i.e., gravity), an interference fit or a friction fit. Regardless of the type of fit, the device no is sized and shaped such that it can be slipped on and off the shopping cart handle 128, or other smaller handles, in the manner described hereinabove.

In operation, two or more handles no can be used on a single shopping cart handle 128 in a side-by-side or spaced-apart arrangement in order to provide more coverage of the contaminated surface and more space for a user to place his or her hands. The handle 110 is also adapted for use with smaller handles, such as those of baggage, briefcases and the like.

The aforementioned "U"-shaped, open-ended design of the device 110 provides it with a curved, crown-like portion 130 and a pair of straight, skirt-like legs 132, 134 depending therefrom in substantially parallel fashion. The cross-sectional shapes (i.e., profiles) of the outer surface 114 and inner surface 126 can be tailored to achieve a variety of design objectives. For instance, when the inner surface 126 has a slight ellipticity (see, for example, FIG. 3 of U.S. provisional patent application 63/019,169, which application has been incorporated herein by reference), rotation about the shopping cart handle 128 will be facilitated. This is due to an inherent reduction of contact area, and consequent reduction of friction between the shopping cart handle 128 and the handle grip 110. Such a shape also enhances a user's ability to adjust the handle grip 110 to the angle of his or her preferred grip position when the handle grip 110 is in use, whether such use is on the shopping cart handle 128 or one of the other (i.e., smaller) handles described hereinabove. In the case of the outer surface 114, a generally elliptical shape may provide superior comfort to a user.

When the user's interaction with the potentially contaminated object has ended, the interface device 110, like the interface device 10, can be removed and sanitized and/or decontaminated for purposes of reuse. As the device no can be decontaminated, unlike other forms of protection, the device no is reusable (i.e., not disposable). In other words, device no is portable and adapted for personalized use by a single individual or a family of users.

In an embodiment, the protective interface devices 10, no can cooperate with one or more complementary accessories that further promote safety and sanitation. Although the devices 10, 110 described hereinabove can be used separately, their use is the most safe and effective when they are used in combination with each other and/or with the following additional components as a complete set/kit.

Figure 14:
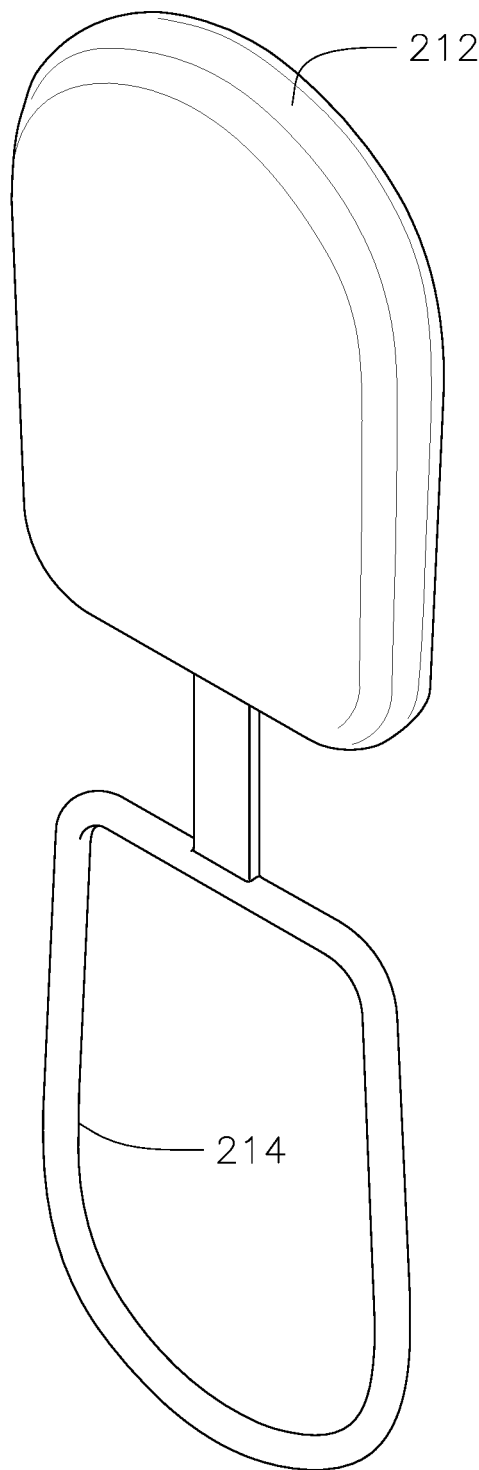
FIG. 14 is a perspective view of the end cap illustrated in FIG. 10.
Figure 15:
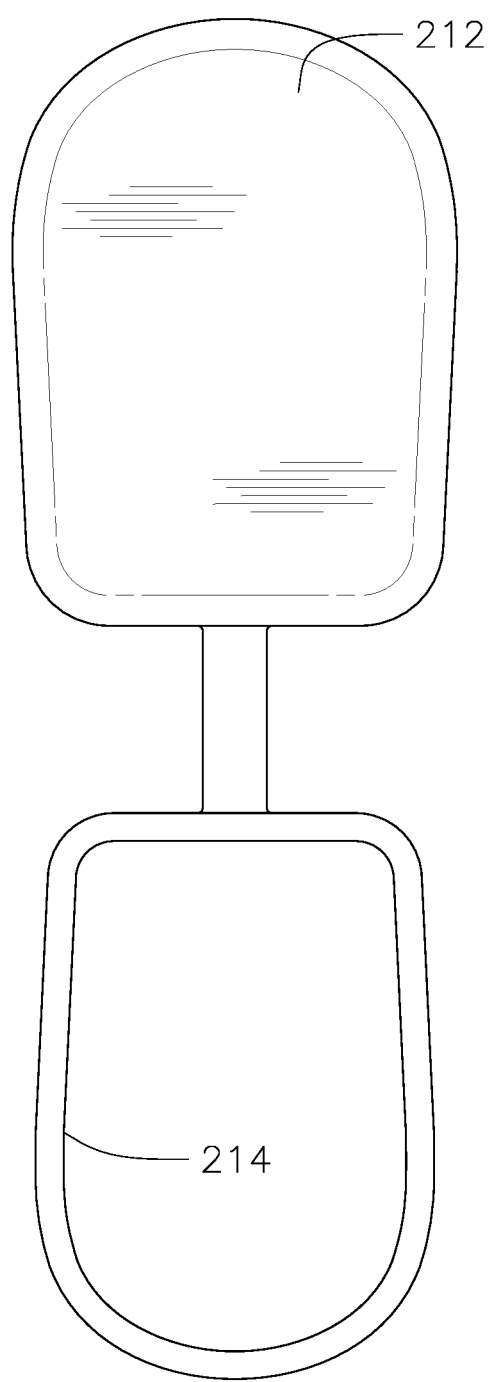
FIG. 15 is a plan view of the end cap of FIG. 14.
Figure 16:
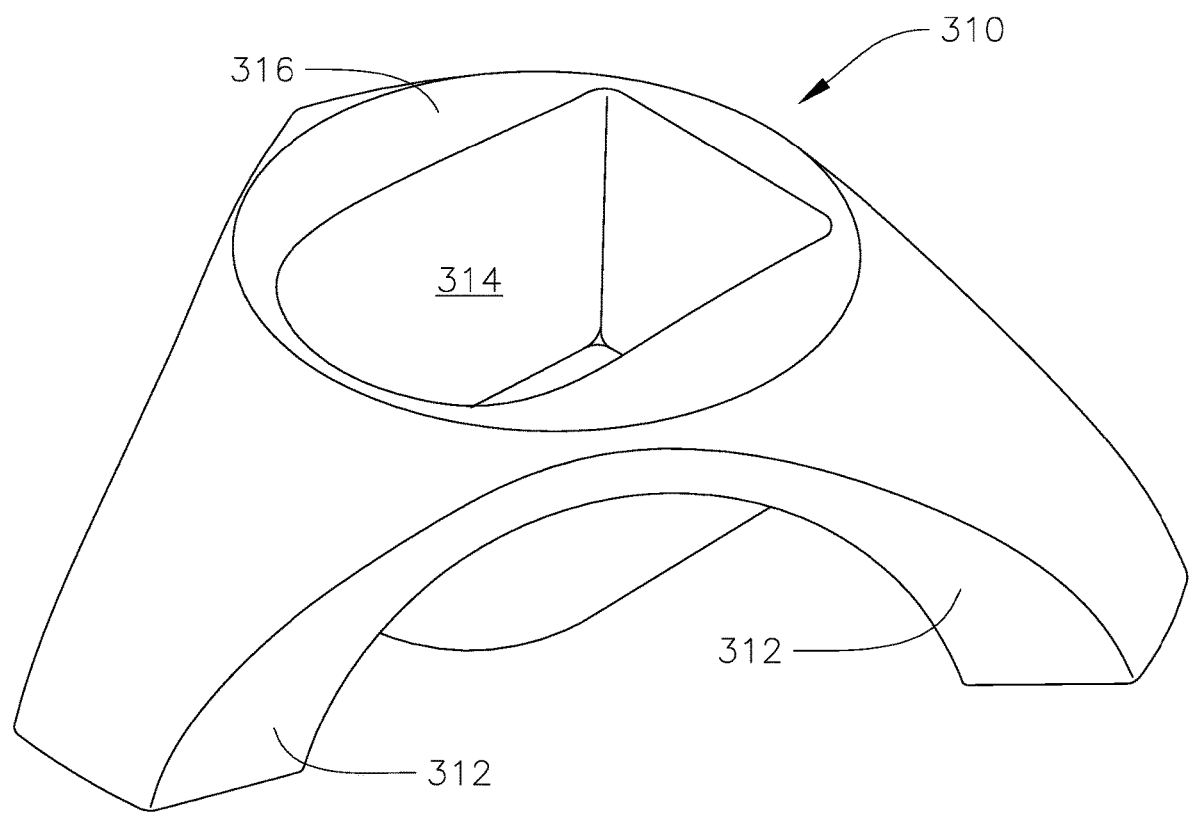
FIG. 16 is a perspective view of a stand configured for use in combination with the case illustrated, fully or partially, in FIGS. 10-15.
Figure 17:
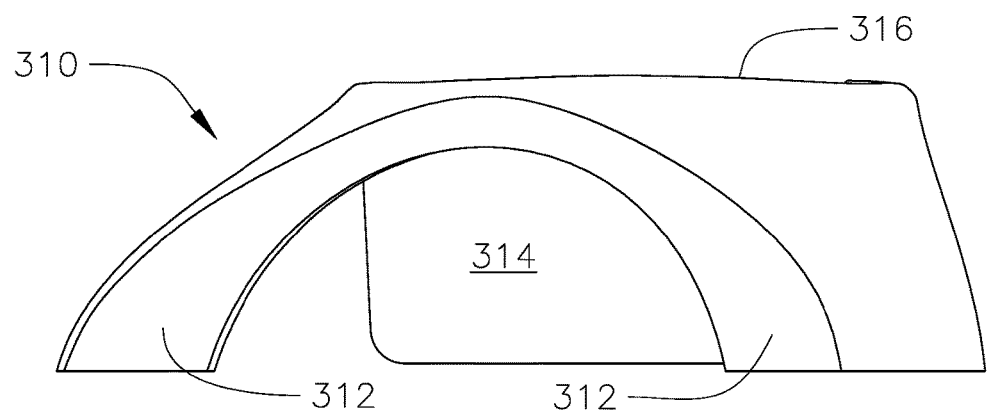
FIG. 17 is a side elevational view of the stand of FIG. 16.
Figure 18:
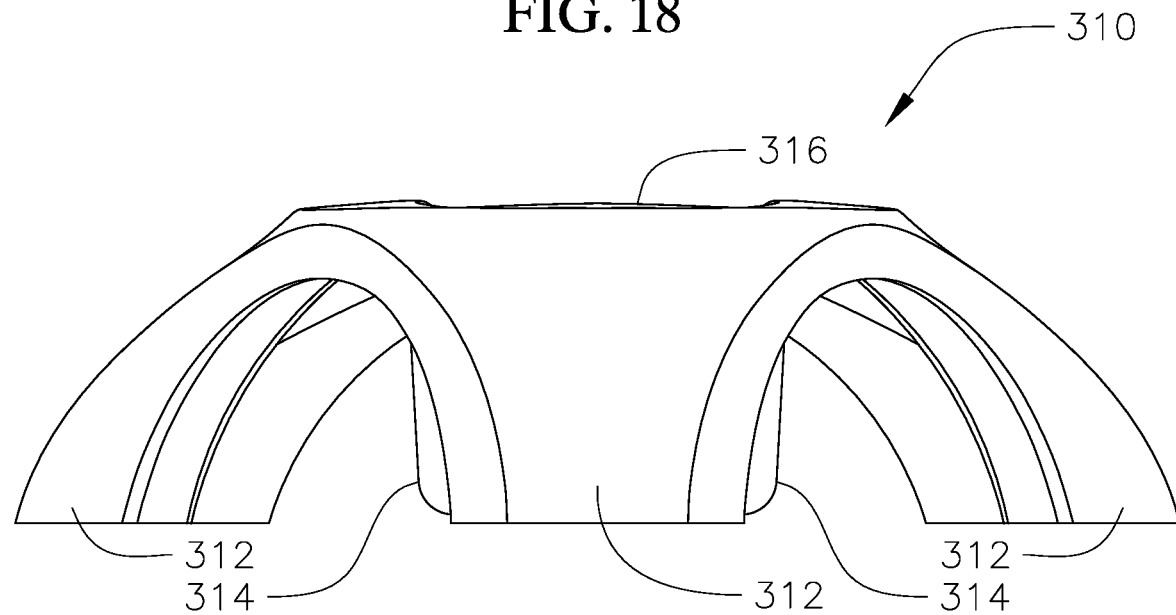
FIG. 18 is an additional side elevational view of the stand of FIG. 16.
Figure 19:
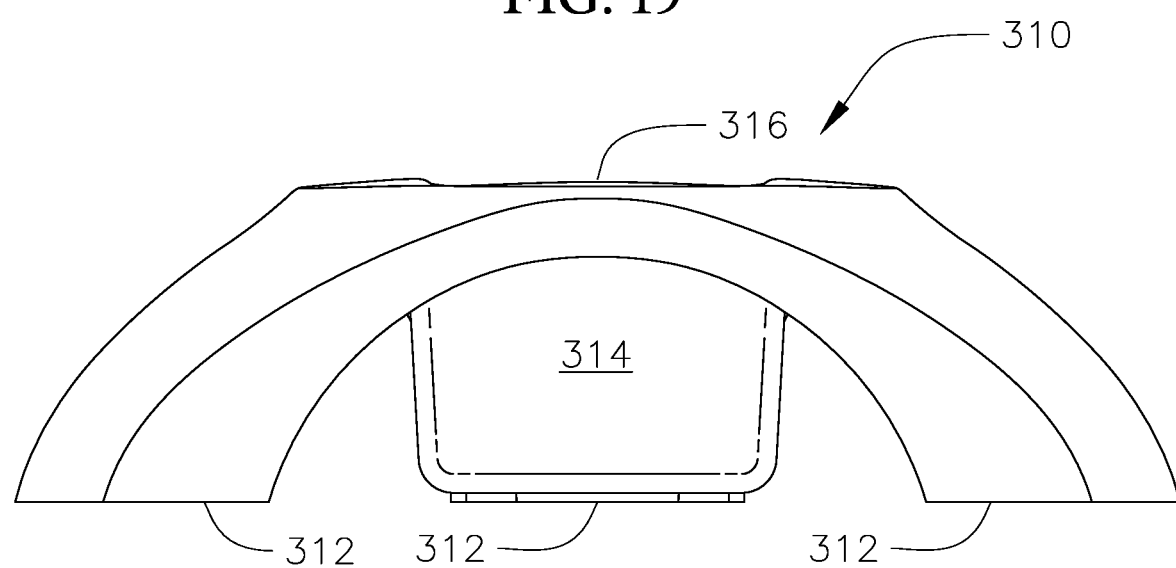
FIG. 19 is a further side elevational view of the stand of FIG. 16.
Figure 20:
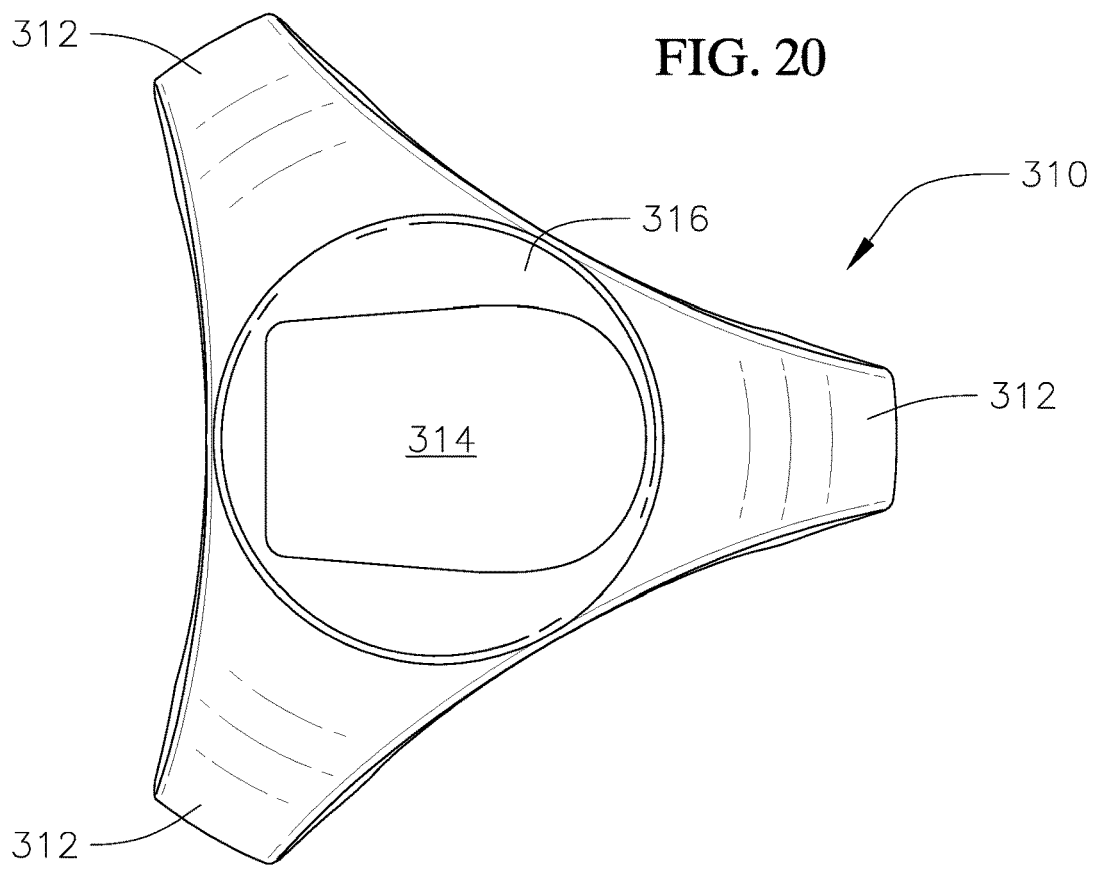
FIG. 20 is a top plan view of the stand of FIG. 16.
Figure 21:
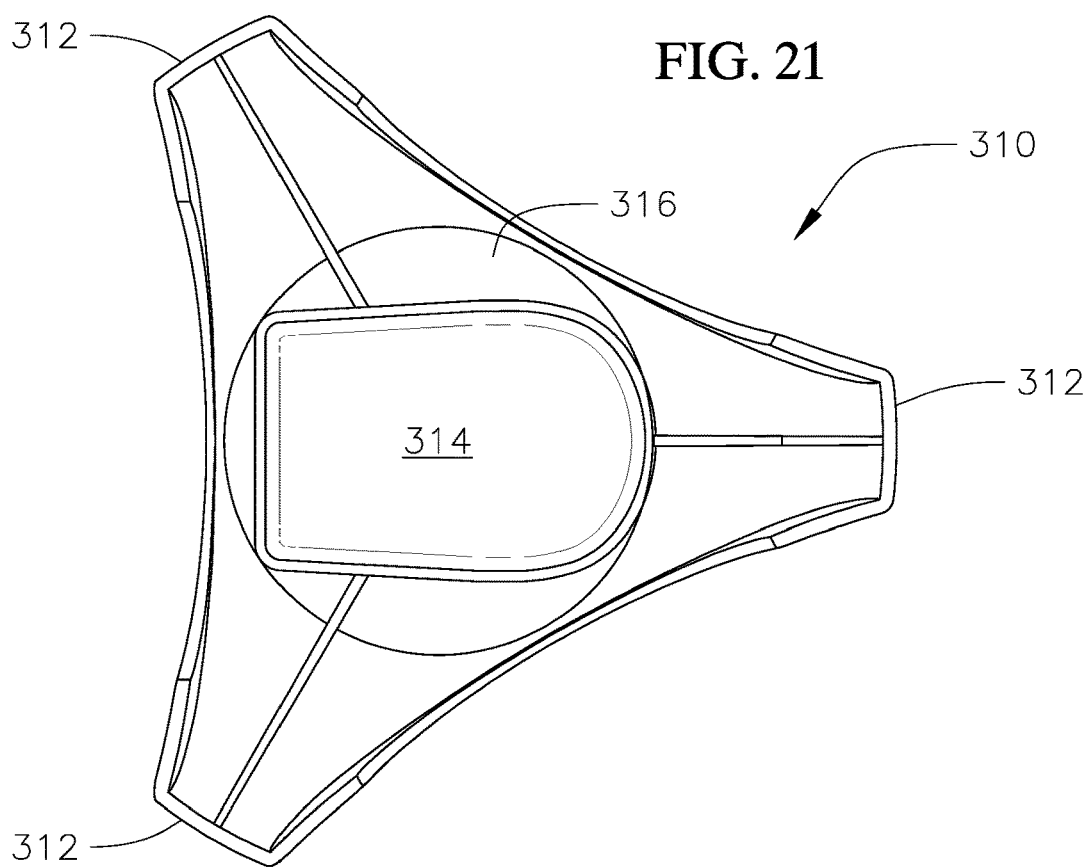
FIG. 21 is a bottom plan view of the stand of FIG. 16.

FIGS. 10-13 depict a carrying/storage/treatment case 210 that functions to enclose one or more of the protective interface devices 10, 110 when they are not in use, thereby providing a further barrier between a user and the potentially contaminated inner surfaces 26, 126 of the devices 10, 110, respectively. To enhance such cleaning functionality and to shield a user from the decontaminating agent and/or energy, the case 210 has a lid 212 (see, especially, FIGS. 14 and 15) that cooperates with an attachment ring 214 adapted for placement around an open end 216 of the case 210. The lid 212, which can be removable together with the attachment ring 214, forms a seal that is resistant to the migration of dust, liquid and/or vapor when the lid 212 is in a closed position on the case 210. Other lid designs (e.g., those disclosed in U.S. provisional patent application Ser. No. 63/019,169, which application has been incorporated herein by reference) can be used as well. An interior chamber 218, which extends from the open end 216 to a closed end (i.e., bottom) 220 of the case 210, is configured to removably receive one or more of the devices 10, 110 through the open end 216 when the lid 212 is in its open position on the case 210.

Figure 10:
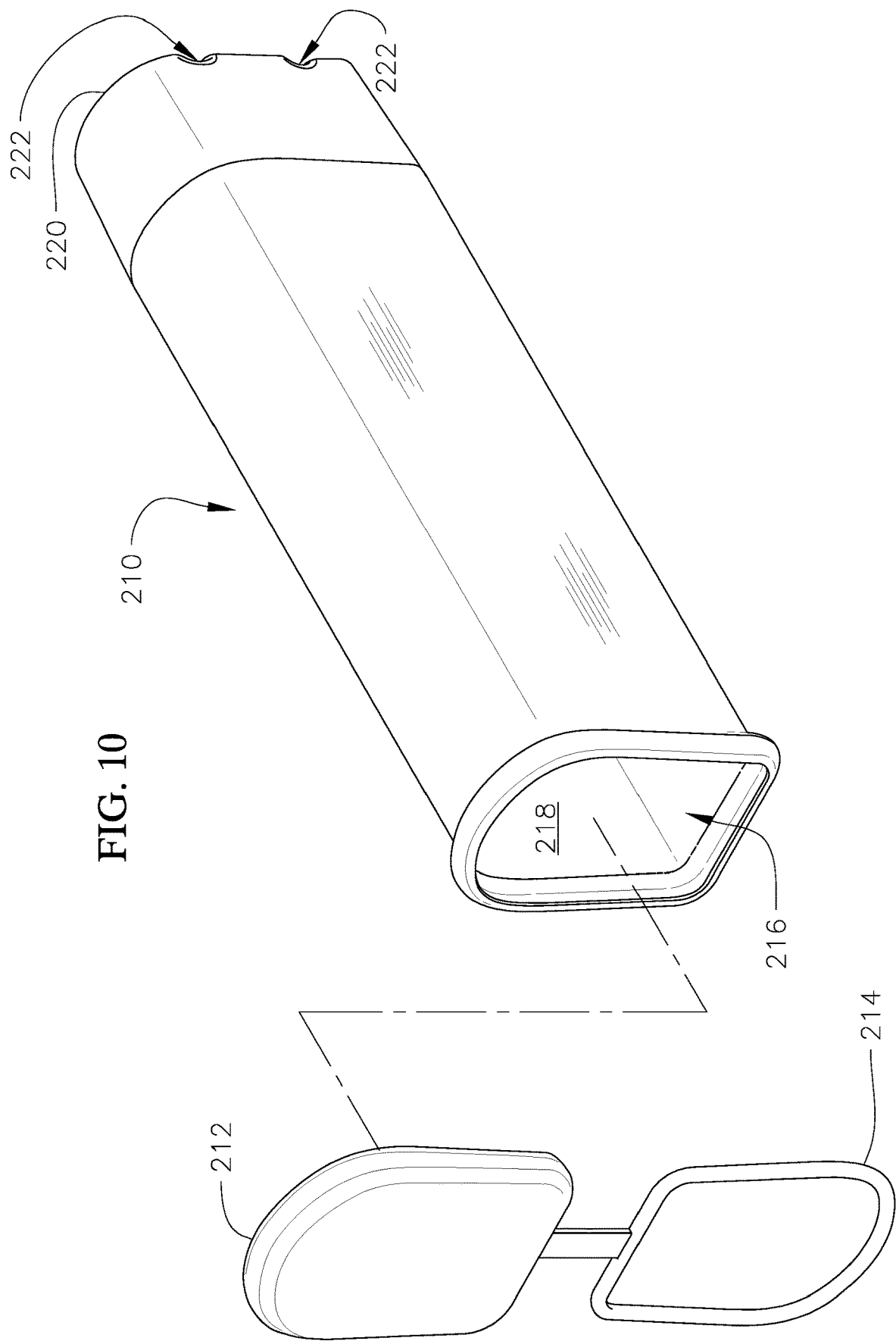
FIG. 10 is an exploded perspective view of a carrying/storage/treatment case and its associated end cap (i.e., lid assembly) configured for use with the handle grips illustrated in FIGS. 1-9.
Figure 11:
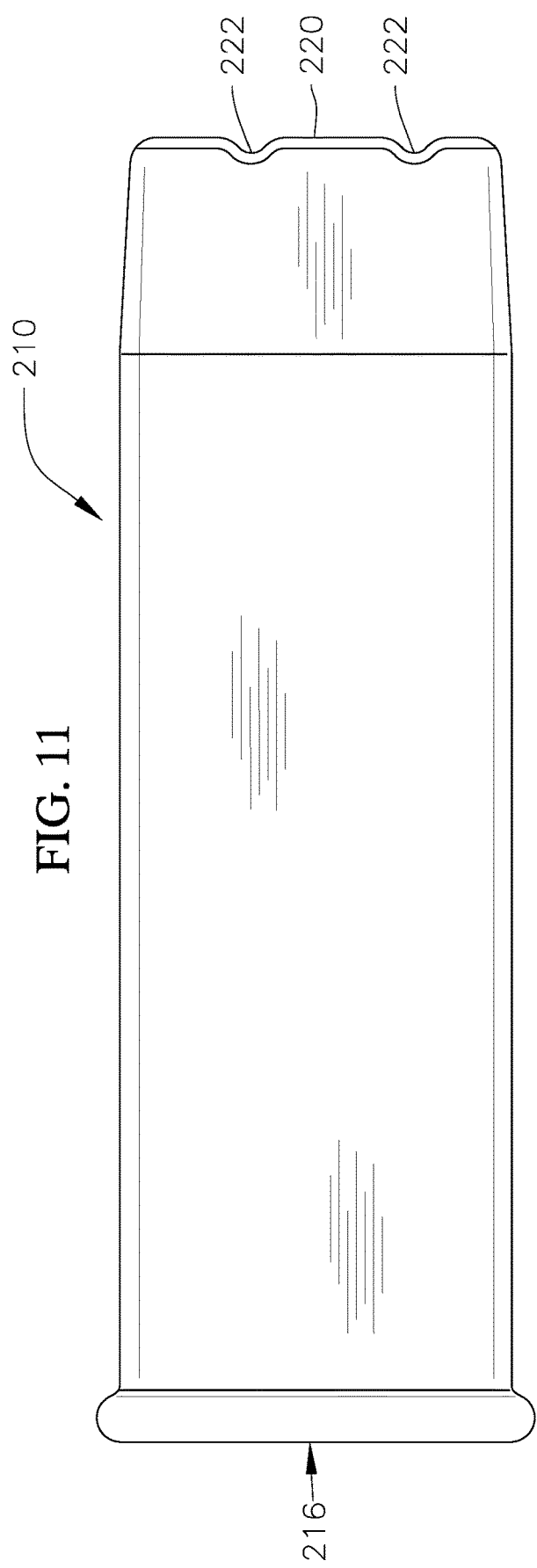
FIG. 11 is a side-elevational view of the case of FIG. 10, with its end cap removed.
Figure 12:
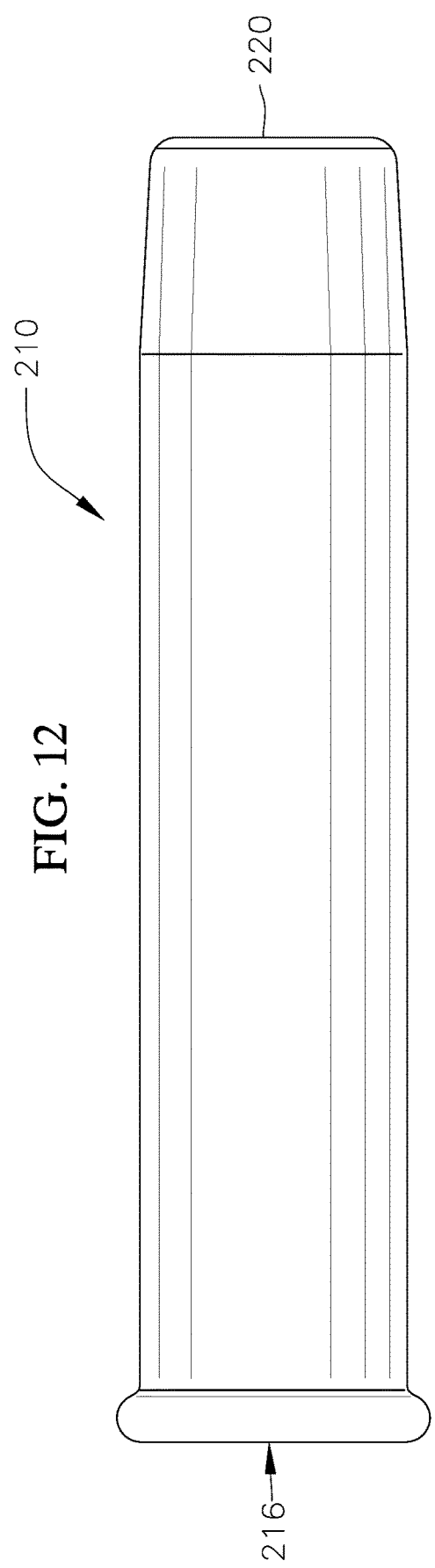
FIG. 12 is a top plan view of the case of FIG. 11.
Figure 13:
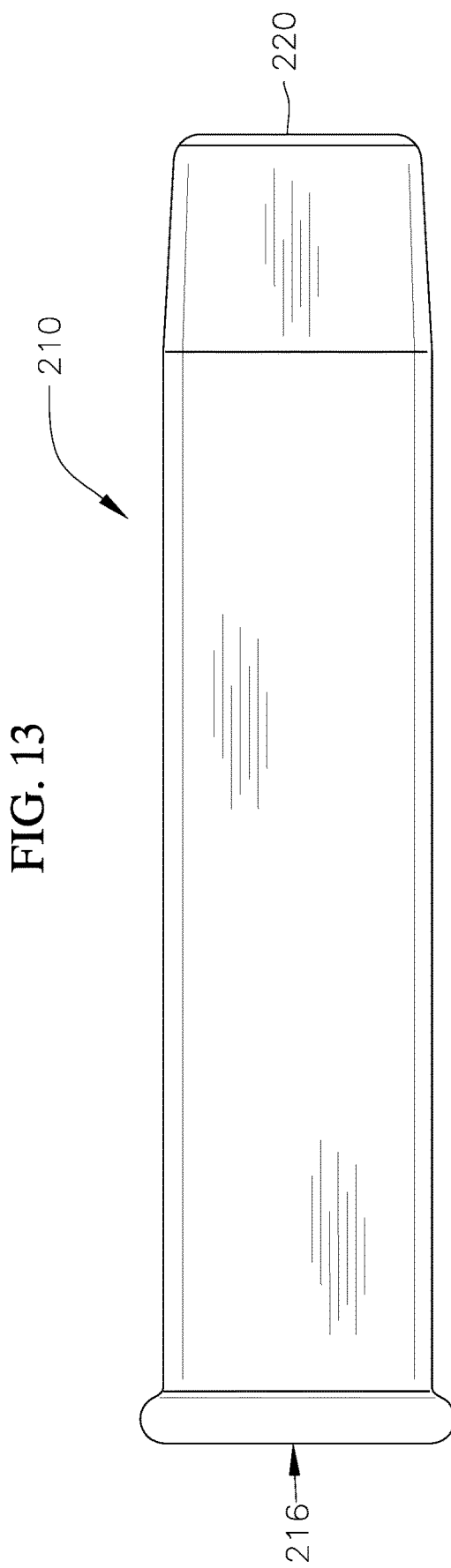
FIG. 13 is a bottom plan view of the case of FIG. 11.
Figure 23:
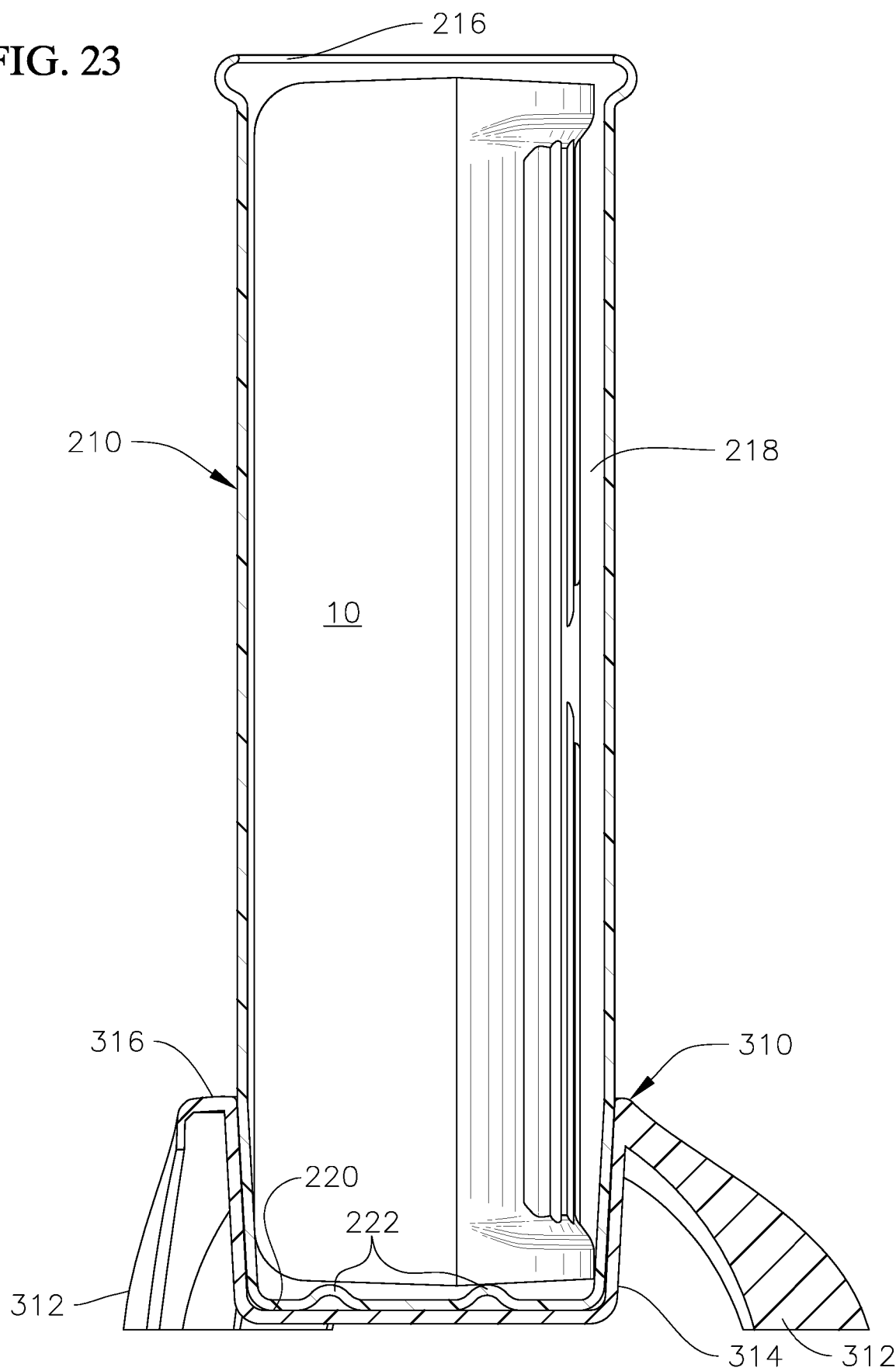
FIG. 23 is a longitudinal cross-sectional view of the stand and case of FIG. 22, the case being shown in combination with a handle grip like the one depicted in FIGS. 1-8.
Figure 24:
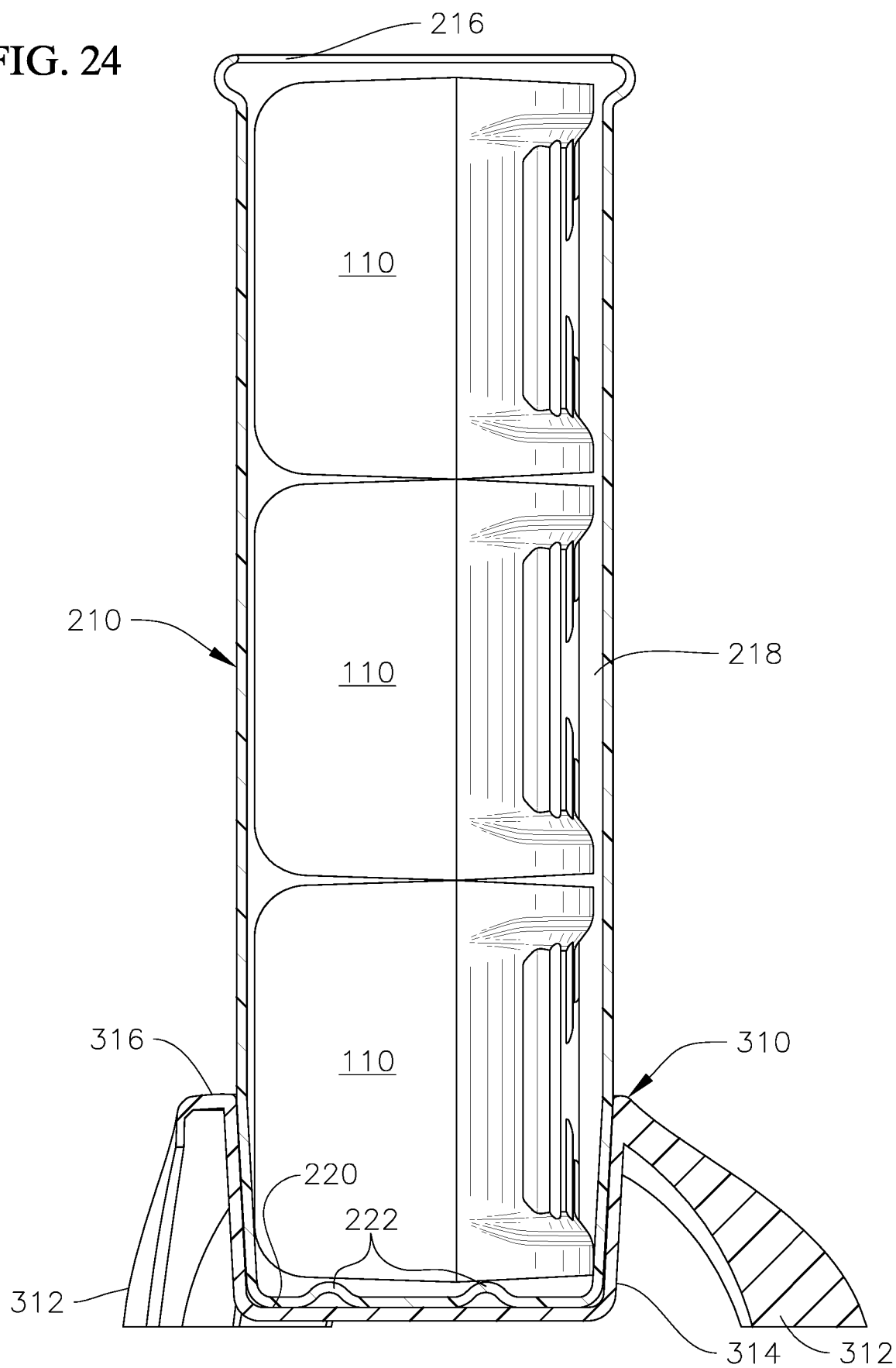
FIG. 24 is a longitudinal cross-sectional view similar to FIG. 23, but showing the case in combination with three of the handle grips shown in FIG. 9.
Figure 25:
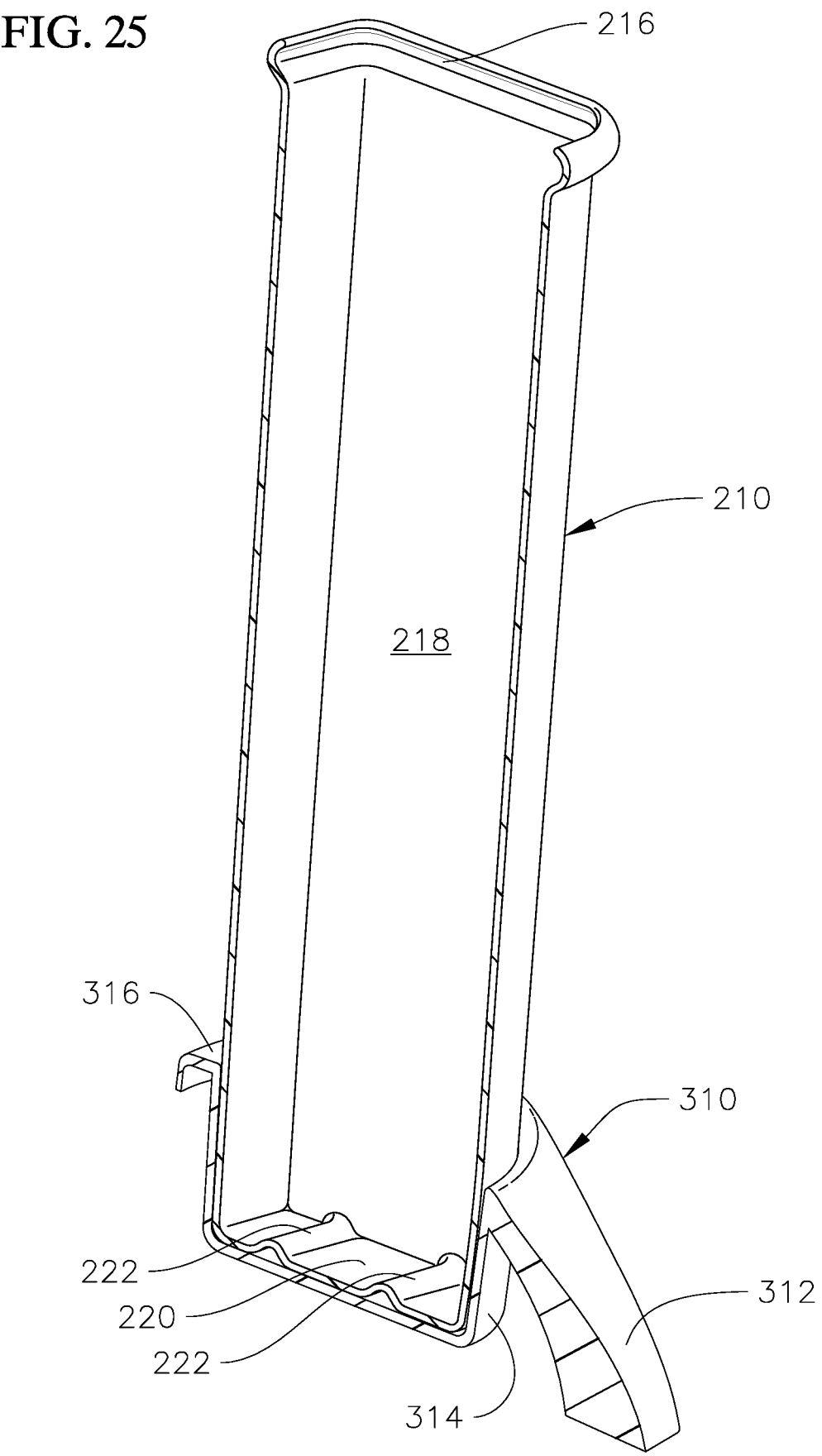
FIG. 25 is a longitudinal cross-sectional view, depicted perspectively, of the case and stand of FIG. 22.

In certain embodiments, the case 210 can function to decontaminate or otherwise treat a stowed interface device 10 and/or one or more of the interface devices 110, which device or devices would be supported in a spaced relationship to the bottom 220 of the case 210 by a pair of rails 222 (shown only partially in FIGS. 10 and 11, but in greater detail in FIGS. 23, 24 and 25). Such functionality could be accomplished through the use of chemical decontaminating agents (e.g., disinfectants, anti-microbial compounds, etc.), or through the use of energy sources (e.g., UV light or other electromagnetic waveforms) effective for the intended treatment.

The case 210 is compact enough to render it portable. For instance, a user could carry the case 210 from place to place by hand. Alternatively, the case 210 could be provided with an optional shoulder strap (not shown) or belt clip (not shown), either fixed or removable, for releasable attachment to a user's belt.

By way of example only, the case 210 could be manufactured from transparent or translucent plastic, or from materials that protect the user from the emittance of targeted radiant energy (e.g., an opaque case material or a lead lining). The case 210 could also be made from a material that permits marking with a user's name or other means for identifying a particular user.

FIGS. 16-21 depict a stand 310 adapted to function as a docking station for the case 210. In the depicted embodiment, the stand 310 has a tripod configuration characterized by legs 312, three of which are shown. The stand 310 is also provided with a well or pocket (i.e., receptacle) 314 configured to interface with the case 210 (see FIG. 16). The well 314 is formed as a depression in a raised platform 316. In other words, the stand 310 in all of its potential forms described herein functions to hold the case 210 in all of its potential forms described herein. The stand 310 can be a clip-on plastic component, or it can take a different shape (e.g., hemispherical, cubic, etc.). The stand 310 can be magnetized on one or more sides for use on unstable metal surfaces such as on ships or planes. In certain embodiments, the stand 310 can be weighted to provide additional stability. Optionally, the stand 310 can also accommodate decorative covers.

Figure 22:
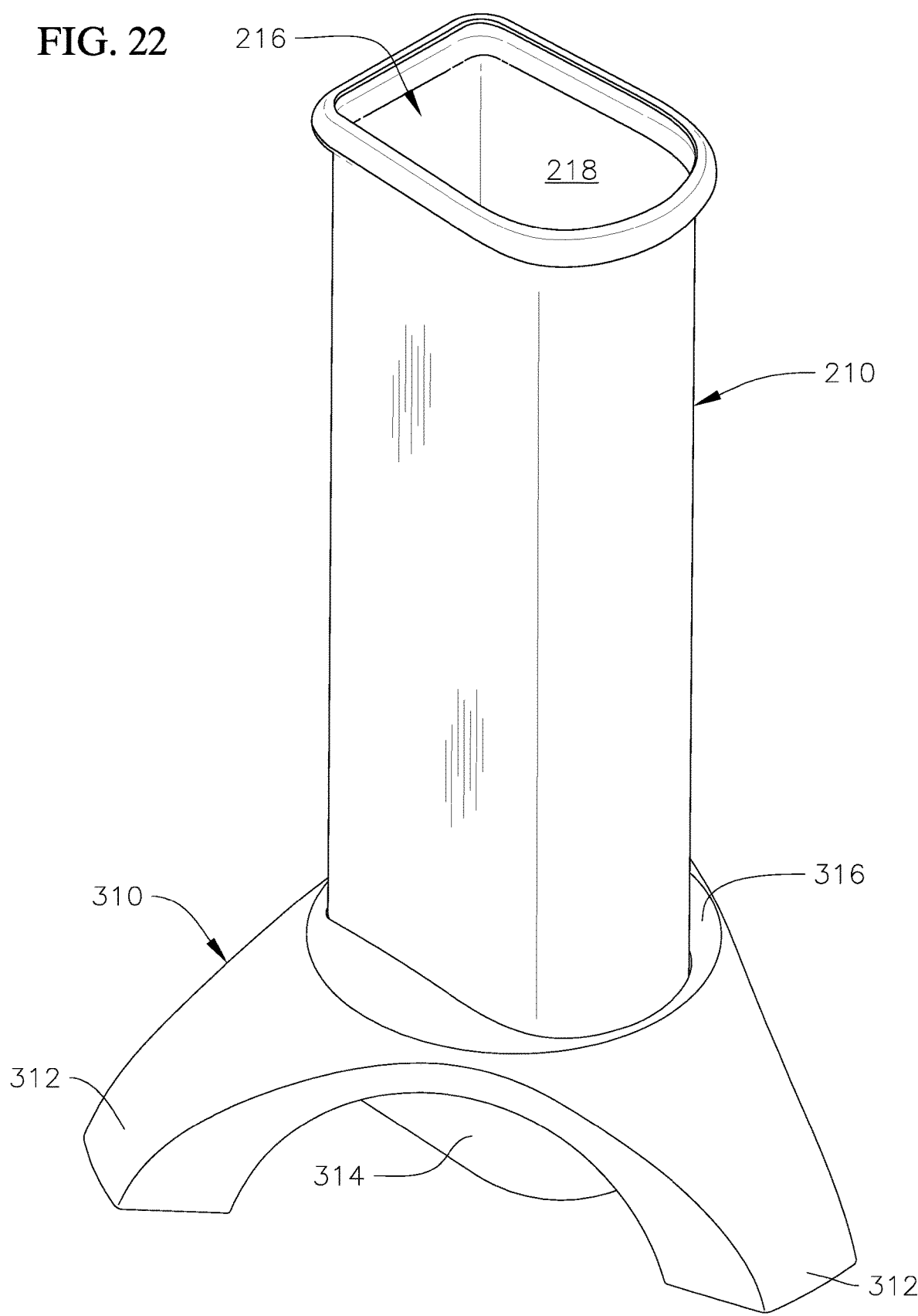
FIG. 22 is a perspective view showing the case of FIG. 11 seated on the stand of FIG. 16.

The stand 310 provides a convenient support and a storage space for the case 210. FIGS. 22-25 show various views of the stand 310 in combination with the case 210, by itself, or in combination with one or more of the handle grips 10, 110. FIG. 22 shows the case 210 (without its lid) mounted in the well 314 of the stand 310 in an upright (i.e., generally vertical) orientation to form a case/stand combination. FIGS. 23, 24 and 25 show cross-sections of the case/stand combination of FIG. 22.

With particular reference to FIG. 23, it shows the aforementioned case/stand combination in further combination with a single one of the handle grips 10 described above, the handle grip 10 being shown in the case 210 which is seated in the stand 310 and the handle grip 10 being supported within the interior chamber 218 of the case 210 by the rails 222. In a similar fashion, FIG. 24 shows the aforementioned case/stand combination in further combination with three of the handle grips no (as described above, the handle grips no are smaller versions of the handle grips 10 and therefore especially adapted for us on the smaller handles common to luggage, briefcases, tool cases, etc.), the handle grips no being shown in the case 210 which is seated in the stand 310 and the handle grips no being supported within the interior chamber 218 of the case 210 by the rails 222.

While FIG. 25 shows the aforementioned case/stand combination without any of the handle grips 10, 110, it more clearly shows the pair of rails 222 running across the closed end (i.e., bottom) 220 of the case 210. As described above, the rails 222 maintain a spacing between the handle grips 10, no and the closed end 220 of the case 210, thereby allowing the stowed handle grips 10, no to minimize their contact with any residual liquid or other flowable decontaminating agents in the bottom 220 of the case 210 until those agents dry.

The stand 310 can be adapted for use either at home or in any type of land, sea or air vehicle. For instance, the stand 310 can be adjustable or otherwise adapted to fit in a conventional cupholder, whether in furniture, a boat, an airplane or a land vehicle (e.g., a car). In an alternate embodiment, the protective interface devices 10, 110 can be directly coupled to the stand 310.

Figure 26:
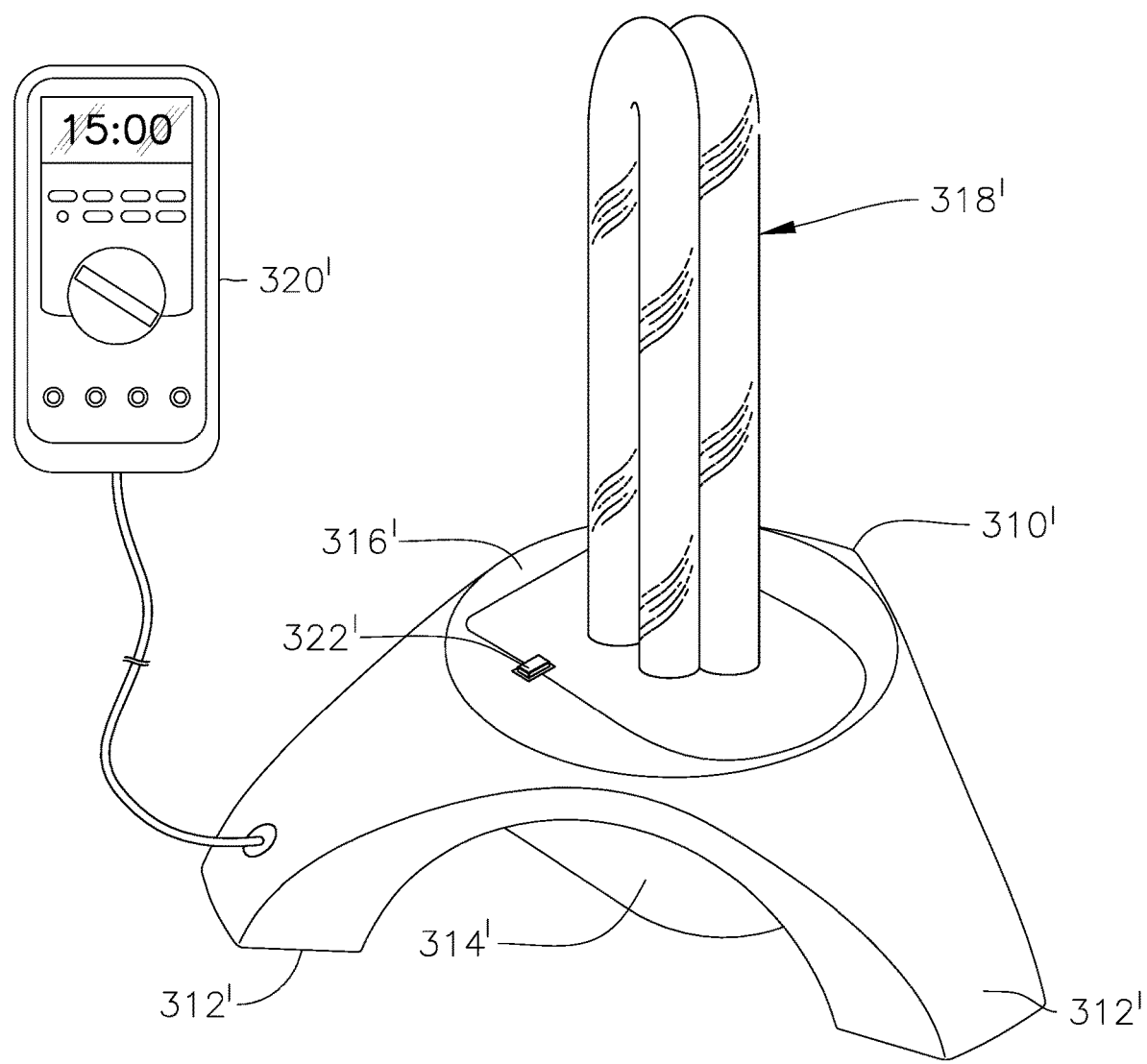
FIG. 26 is a perspective view of a modified embodiment of the stand illustrated in FIGS. 16-21, the modified stand including a UV radiation element.
Figure 27:
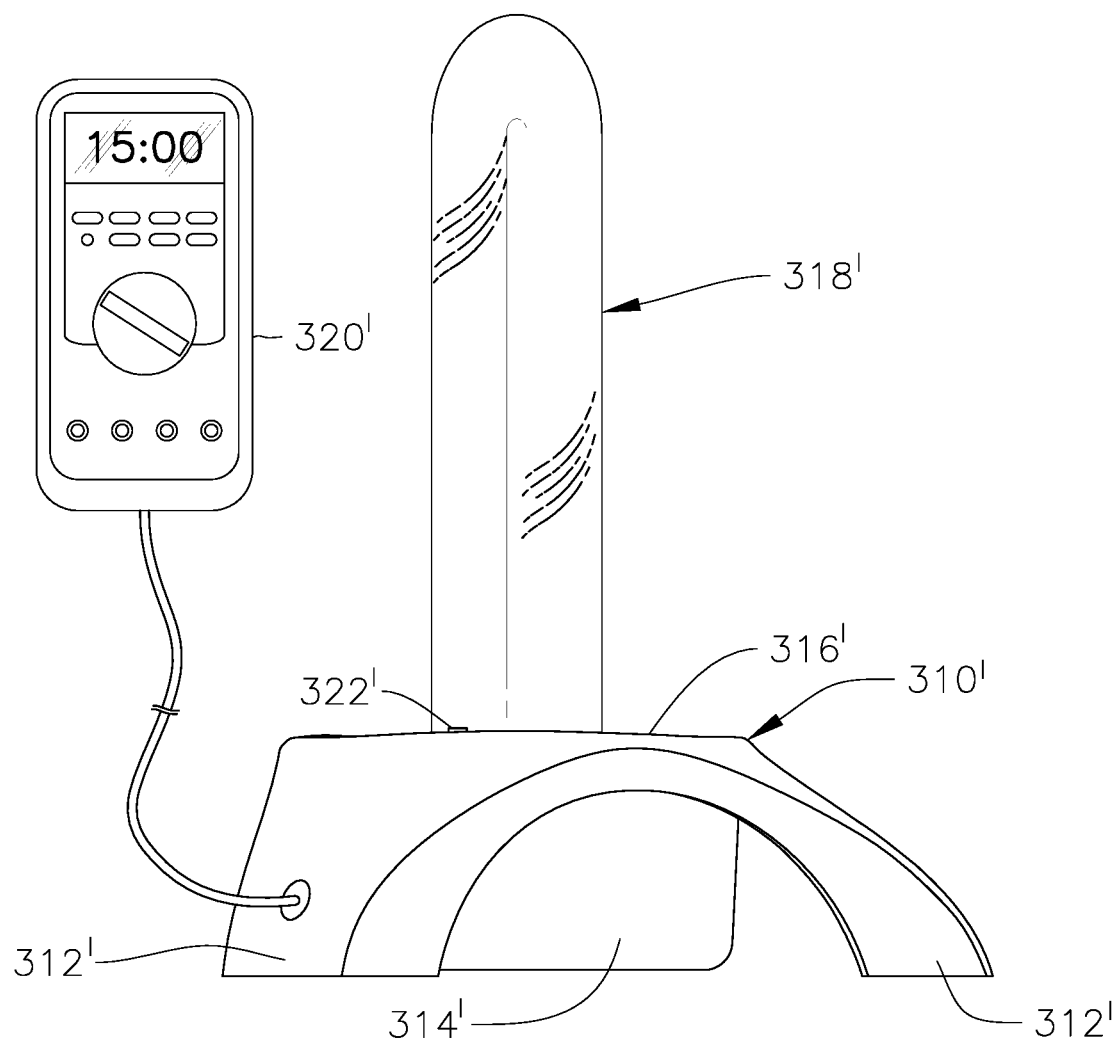
FIG. 27 is a side-elevational view of the stand of FIG. 26.

The stand 310 can include decorative LED lighting, whereby a tradename or an associated decontamination agent or energy source can be spelled out for visual inspection. Further electronic or non-electronic (e.g., mechanical) display means can display information regarding the status of the system (i.e., the interface device(s) 10, 110; the case 210; and/or the stand 310), such as the current contamination state of the interface device(s) 10, 110 or the status of the decontamination agent or energy source being employed within the case 210. To that end, a timer (see FIG. 26) or a sensor (e.g., a radiation exposure meter, not shown) can be integrated with the stand 310.

If electrically powered, features that enhance user utility can be incorporated in the stand 310. Such features can include speakers for music, a communication device (e.g., interface means to smart speakers, a two-way radio, etc.), a night light, a security device and internet-connectable devices for monitoring or controlling the status and functions of the stand 310 as well as its associated case and/or interface device (i.e., kit), etc.

The stand 310 and the case 210 can be sold individually (i.e., separately), or they can be sold and packaged as a set or kit along with the protective interface devices 10, 110. Whether sold individually or as part of a kit, the protective interface devices 10, 110 offer the user the benefit of multiple applications without delay and without possible contamination from its exposed interior surface (i.e., the inner surfaces 26, 126). By way of example only, using one hand only, a user can remove the interface device 10, for instance, from its case 210, open a building door with tubular door handles, apply the device 10 underneath the two handles of a shopping basket, and then, without releasing or changing the device 10, the user can place a shopping basket in the cart (if the items to be carried become too cumbersome), relocate the device 10 to the cart handle, push the cart, slip the device 10 off the cart handle and use it to open a freezer door or a refrigerated beverage case door, reapply the device 10 to the shopping cart handle, remove the device 10 from the shopping cart handle and use the device 10 to exit a building without directly touching the tubular door handles, and then place the device 10 back in its case 210. The aforementioned activities can all of be done in a continuous sequence without releasing the device 10 or touching its potentially contaminated inner (i.e., exposed) surface 26. Upon returning to the user's home, or other location at which an associated stand (e.g., the stand 310) is situated, the case 210 can be placed in the stand 310 and the lid 212 opened so that disinfectant can be sprayed or otherwise introduced into interior chamber 218 of the open case 210. All of the foregoing activities can be undertaken without touching the potentially contaminated inner surface 26 of the device 10.

When forming part of a kit, the case 210 may be provided as a pair for optimal utility (i.e., one case for holding a previously decontaminated handle grip 10 and the other case for docking on the stand 310 for decontamination). Like the case 210, the stand 310 can contain an electric power source (not shown), either in lieu of or in conjunction with any compatible power source provided on the case 210. The power source, if provided in conjunction with the stand 310, could function to power electronic elements on the case 210 (if any) and/or on the stand 310 itself. To that end, the stand 310 could be provided with batteries, power from a receptacle, or power from a conventional electrical outlet.

In a modified embodiment illustrated in FIGS. 26-30, stand 310' is equipped with a UV radiation source 318', such as TEPRO CUH-18L UV-C Lamp with a 2G11 base. When UV radiation is used as the decontamination agent, a quartz glass or other UV transmissive material (not shown) may be incorporated into the case 210 and/or stand 310' to provide the UV radiation source 318' with protection against physical impact. In order to interface with the UV radiation source 318', the case 210 can have an opening (not shown) in its bottom 220. Alternatively, a plug, latch, door or other mechanism can be used to selectively open and close the bottom 220 of the case 210. Alternately, the case 210 can also be inverted and placed over the UV radiation source 318' after opening the lid 212.

Figure 29:
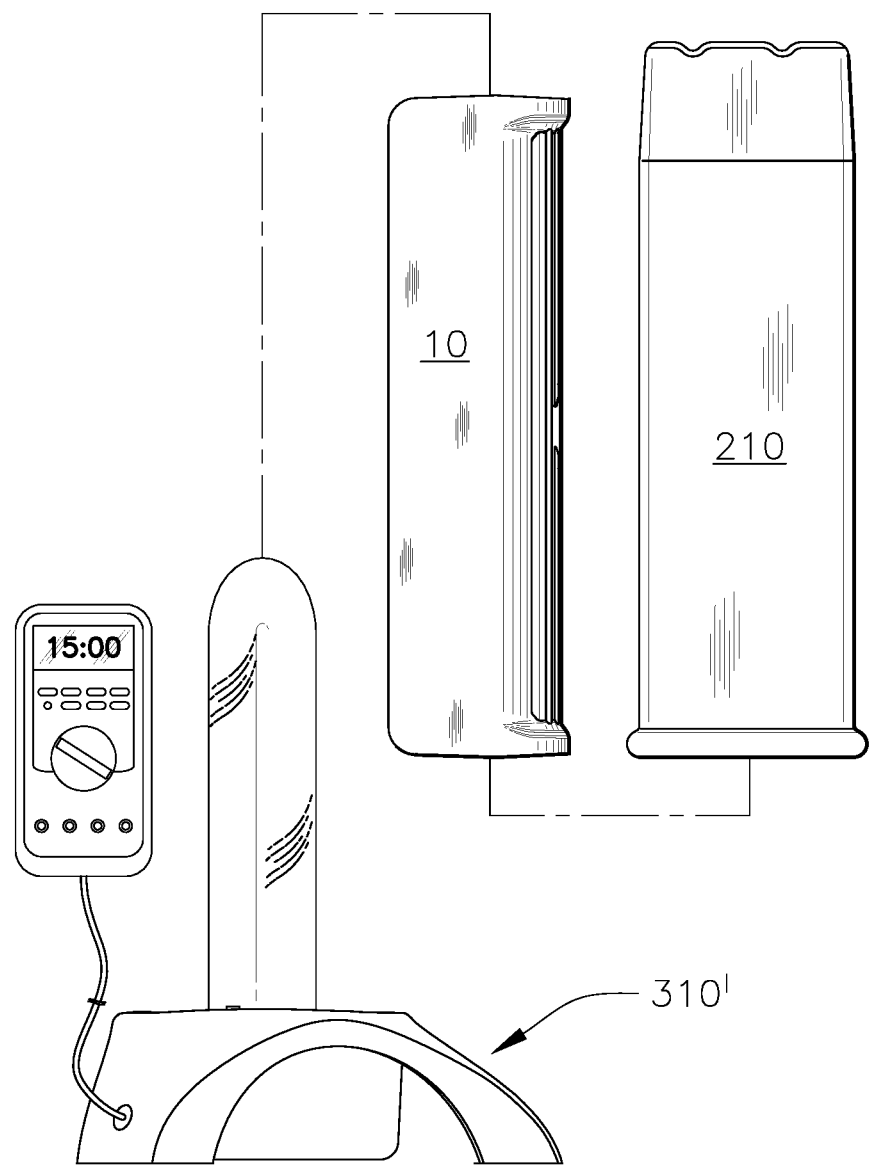
FIG. 29 is an exploded view of the stand of FIG. 27 in combination with the handle grip of FIGS. 1-8 and the case of FIGS. 11-14.

When the case 210 is mounted on the modified stand 310', the UV radiation source 318' can be electronically actuated for the purpose of sanitizing, decontaminating, disinfecting and/or otherwise treating the device 10 and the interior chamber 218 of the case 210 prior to further use (see FIG. 29). For instance, the UV radiation source 318' can be actuated via the coordinated operation of a disconnecting means (i.e., plug), a timer 320' and a proximity safety switch 322' (see FIG. 28), which can be located on platform 316' of the modified stand 310'. The safety switch 322' also provides an additional means to avoid accidental operation of the UV radiation source 318' when the case 210 is not covering the UV radiation source 318' to thereby shield the user from UV radiation emitted by the UV radiation source 318'.

Although an optional feature of the modified stand 310', the timer 320' can be adapted to monitor, track and/or regulate any decontamination functions performed by the UV radiation source 318' associated with the stand 310'. In accordance with other optional features, the modified stand 310' could include a power source (not shown) adapted to power any associated electrical or electronic features of the stand 310' and/or its associated case 210.

Multiple stands can be used to hold multiple cases, or a single stand can be provided to hold multiple cases in the event the needs of more than one family member or employee require concurrent use of more than one of the handle grips 10, 110. Multiple stands, or a stand adapted to work with more than one case, may also be useful when different sources of contamination require different contaminating agents or energies. When provided as a kit, the case 210, stand 310 and one or more of the handle grips 10, 110 operate to protect the user at all times through insulation and decontamination.

Figure 31:
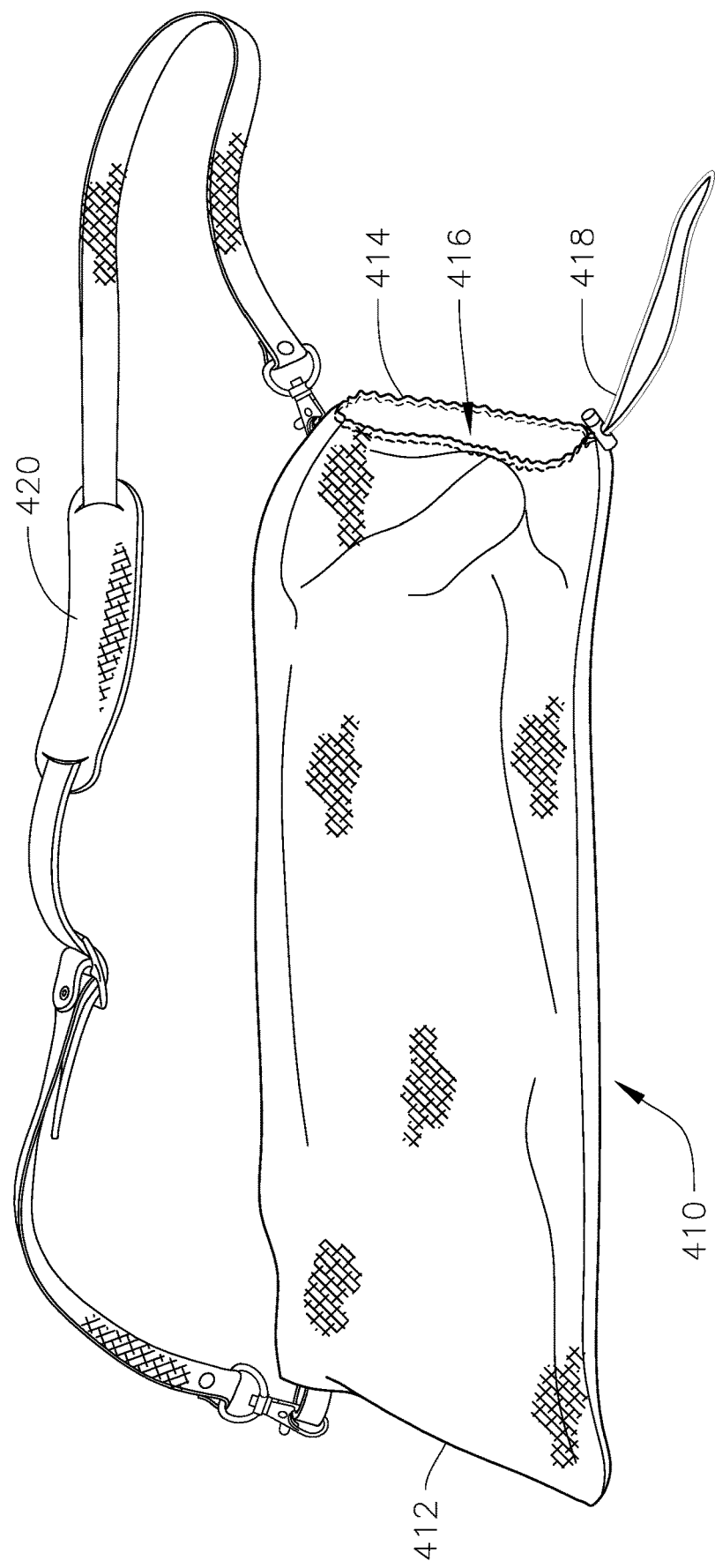
FIG. 31 is a perspective view of a satchel configured for use with the case illustrated in FIGS. 10-15.

With reference to FIG. 31, the kit depicted in FIGS. 22-25, or the one depicted in FIG. 29, can further include a satchel 410 adapted to transport one or more of the cases 210 (not shown) between a point of use (e.g., at a supermarket, big box retailer, etc.) and a destination location, such as a destination where the stand 310 or 310' resides. The satchel 410, which can be made from any suitable fabric or any other conventional material commonly used to make backpacks, gunnysacks or the like (e.g., canvas), has a closed end 412, an open end 414 and an interior compartment 416, which is accessed through the open end 414 and is configured to receive at least one of the cases 210. The open end 414 of the satchel 410 can be selectively closed by drawstrings 418, or any other known conventional means (e.g., clips, buckles, latches, magnets, hook and loop fasteners, etc.). When pulled, drawstrings 418 collapse the open end 414 of the satchel 410 to secure the case or cases 210 inside the interior compartment 416. For a user's convenience, a shoulder strap 420 is provided on the satchel 410, thereby enhancing its portability and freeing a user's hands for other activities, such as the handling of handle grips 10, 110 as described above. In a similar fashion, the portability and handling of each of the cases 210 could be enhanced by providing it with its own shoulder strap or hand strap (not shown).

It will be understood that the embodiments described hereinabove are merely exemplary and that a person skilled in the art may make many variations and modifications without departing from the spirit and scope of the present invention. All such variations and modifications are intended to be included within the scope of the invention as defined in the appended claims.

The invention claimed is:

1. A multi-positionable handle grip for interchangeable use with a plurality of different handles, said handle grip comprising a substantially rigid, trough-shaped body having a pair of open ends on opposite sides of said body, which has a generally U-shaped configuration, said body extending linearly between said open ends thereof, said body also having an outer surface grippable by a user and an inner surface configured to be at least partially contactable with a potentially contaminated handle, said outer and inner surfaces of said body being defined by a pair of substantially straight and substantially parallel legs extending from opposite sides of a central body section bridging between the legs of said pair of legs, said legs being spaced apart along their entire lengths and terminating remote from said central body section in non-deflectable free ends, respectively, which cooperate to define an open mouth of a predetermined, substantially fixed and constant dimension selected to permit said handle grip to be applied to and removed from a potentially contaminated handle by a user without wrapping said legs there around and without increasing said dimension of said mouth, said lengths of said legs are selected so as to inhibit a user and/or third party from contacting a potentially contaminated handle to which said handle grip is applied; and wherein said inner surface of said body extends in a continuous, uninterrupted manner between said open ends of said body of said handle grip.

2. The handle grip of claim 1, wherein said body is elongated and said inner surface thereof has a lateral cross-sectional shape that is non-conforming with respect to an outer cross-sectional shape of a potentially contaminated handle to which said handle grip is applied.

3. The handle grip of claim 2, wherein said lateral cross-sectional shape of said inner surface of said body is configured to present a cam-like profile to a handle to which said handle grip is applied.

4. The handle grip of claim 2, wherein said lateral cross-sectional shape of said inner surface of said body has a radius which is larger than that of a handle to which said handle grip is applied.

5. The handle grip of claim 2, wherein said lateral cross-sectional shape of said inner surface of said body has a radius that is substantially the same as that of a handle to which said handle grip is applied.

6. The handle grip of claim 2, wherein said lateral cross-sectional shape of said inner surface of said body is generally flat compared to a generally curved outer shape of a handle to which said handle grip is applied.

7. The handle grip of claim 2, wherein said lateral cross-sectional shape of said inner surface of said body is generally curved compared to a generally flat outer shape of a handle to which said handle grip is applied.

8. The handle grip of claim 2, wherein said lateral cross-sectional shape of said inner surface of said body is generally elliptical.

9. The handle grip of claim 2, wherein the lengths of said legs are selected so as to position said mouth remote from a potentially contaminated handle to which said handle grip is applied.

10. The handle grip of claim 2, wherein said body is movable in a lateral direction relative to a handle to which said handle grip is applied.

11. The handle grip of claim 10, wherein said body is movable in a longitudinal direction relative to a handle to which said handle grip is applied.

12. The handle grip of claim 11, wherein said body is rotatable relative to a handle to which said handle grip is applied.

13. The handle grip of claim 12, wherein only portions of said inner surface of said body are contactable with a handle to which said handle grip is applied.

14. The handle grip of claim 13, wherein said inner surface of said body has a first contactable portion configured to be contacted by a handle to which said handle grip is applied, said first contactable portion forming part of said central body section; a second contactable portion configured to be contacted by a handle to which said handle grip is applied, said second contactable portion forming part of one of said legs; and a third contactable portion configured to be contacted by a handle to which said handle grip is applied, said third contactable portion forming part of the other of said legs.

15. The handle grip of claim 14, wherein said inner surface of said body is configured such that said first, second and third contactable portions thereof are simultaneously contactable with a handle to which said handle grip is applied.

16. The handle grip of claim 14, wherein said inner surface of said body is configured such that said first, second and third contactable portions thereof are independently contactable with a handle to which said handle grip is applied.

17. The handle grip of claim 14, wherein, in one position of said handle grip relative to a handle to which said handle grip is applied, only said first and second contactable portions of said body are contactable with the handle; and wherein, in another position of said handle grip relative to a handle to which said handle grip is applied, only said first and third contactable portions are contactable with the handle.

18. The handle grip of claim 2, wherein said lateral cross-sectional shape of said inner surface of said body is generally U-shaped.

19. The handle grip of claim 18, wherein said body and said outer surface thereof have lateral cross-sectional shapes that are generally U-shaped.

20. The handle grip of claim 19, wherein said handle grip is useable with some types of horizontally oriented handles when said mouth is oriented upward and with other types of horizontally oriented handles when said mouth is oriented downward; and wherein said handle grip is useable with vertically oriented handles when said mouth is oriented sideways.

21. The handle grip of claim 1, wherein said handle grip is useable with some types of horizontally oriented handles when said mouth is oriented upward and with other types of horizontally oriented handles when said mouth is oriented downward; and wherein said handle grip is useable with vertically oriented handles when said mouth is oriented sideways.

22. The handle grip of claim 21, wherein said body has a center of gravity located such that said body is biased toward an orientation in which said mouth is oriented downward when said handle grip is applied to the other types of horizontally oriented handles.

23. The handle grip of claim 1, wherein said body of said handle grip has a one-piece construction.

24. The handle grip of claim 23, wherein said body of said handle grip is formed monolithically.

25. The handle grip of claim 1, wherein said body of said handle grip is made from a substantially fixed-shape material.

26. The handle grip of claim 25, wherein said substantially fixed-shape material is PET, PETG or other chemically resistant thermoplastic.

27. A method of gripping a plurality of different handles without a user physically contacting any of the handles, said method comprising the steps of:
   i) providing a handle grip having a substantially rigid, trough-shaped body which has a pair of open ends on opposite sides of said body and a generally U-shaped configuration defined by a pair of substantially straight and substantially parallel and non-deflectable legs whose free ends cooperate to form an open mouth of a predetermined, substantially fixed and constant dimension selected to permit said handle grip to be applied to and removed from a plurality of different handles by a user without wrapping said legs there around and without increasing said dimension of said mouth, said body extending linearly between said open ends thereof, said body also having an inner surface which extends in a continuous, uninterrupted manner between said open ends of said body of said handle grip;
   ii) applying said handle grip to a first handle, which is horizontally oriented, such that said mouth of said handle grip is in a downward facing orientation;
   iii) removing said handle grip from said first handle;
   iv) applying said handle grip to a second handle, which is horizontally oriented, such that said mouth of said handle grip is in an upward facing orientation;
   v) removing said handle grip from said second handle;
   vi) applying said handle grip to a third handle, which is vertically oriented, such that said mouth of said handle grip is in a sideways facing orientation; and
   vii) removing said handle grip from said third handle, wherein steps ii), iv) and vi) are not performed in any particular order relative to one another.

28. The method of claim 27, wherein said body of said handle grip has a one-piece construction.

29. The method of claim 28, wherein said body of said handle grip is formed monolithically.

30. The method of claim 27, wherein said body of said handle grip is made from a substantially fixed-shape material.

31. The method of claim 30, wherein said substantially fixed-shape material is a chemically resistant thermoplastic.

* * * * *